United States Patent
Hansen et al.

(10) Patent No.: US 12,178,740 B2
(45) Date of Patent: *Dec. 31, 2024

(54) LEAKAGE DETECTION IN AN OSTOMY DEVICE

(71) Applicant: Coloplast A/S, Humlebaek (DK)

(72) Inventors: Jais Ask Hansen, Jaegerspris (DK); Lars Erup Larsen, Stenloese (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/143,645

(22) Filed: May 5, 2023

(65) Prior Publication Data

US 2023/0301818 A1    Sep. 28, 2023

Related U.S. Application Data

(63) Continuation of application No. 16/955,057, filed as application No. PCT/DK2018/050407 on Dec. 20, 2018, now Pat. No. 11,679,021.

(30) Foreign Application Priority Data

Dec. 22, 2017  (DK) .......................... PA 2017 70984
Dec. 22, 2017  (DK) .......................... PA 2017 70998
Feb. 20, 2018  (DK) .......................... PA 2018 70100

(51) Int. Cl.
    *A61F 5/443*   (2006.01)
    *A61F 5/44*    (2006.01)
    (Continued)

(52) U.S. Cl.
    CPC ............ *A61F 5/443* (2013.01); *A61F 5/4404* (2013.01); *A61F 5/445* (2013.01); *A61L 24/0031* (2013.01)

(58) Field of Classification Search
    CPC .......... A61F 5/4404; A61F 5/443; A61F 5/44; B29C 65/48
    See application file for complete search history.

(56) References Cited

U.S. PATENT DOCUMENTS 2,054,535 A   9/1936  Diack
2,327,514 A * 8/1943  Fenwick ................. A61F 5/445
                                                   604/338
(Continued)

FOREIGN PATENT DOCUMENTS

CA        2202199 C    8/2006
CN     203786580 U    8/2014
(Continued)

OTHER PUBLICATIONS

International Preliminary Report on Patentability received for PCT Patent Application No. PCT/DK2019/050243, mailed on Feb. 25, 2021, 12 pages.

(Continued)

*Primary Examiner* — Guy K Townsend
(74) *Attorney, Agent, or Firm* — Coloplast Corp., Coloplast A/S; Nick Baumann

(57) ABSTRACT

A sensing accessory for detecting leakage in an ostomy device includes a sensor region. The sensor region has a plurality of electrodes providing a plurality of sensors arranged around a stoma-receiving opening. Each of the plurality of electrodes is arranged at a different radial distance from the stoma-receiving opening. A connector is connected at a first end to the plurality of electrodes and extends to a second terminal end that is configured for electrical connection to an external monitor device.

18 Claims, 16 Drawing Sheets

(51) Int. Cl.
*A61F 5/445* (2006.01)
*A61L 24/00* (2006.01)

(56) References Cited

U.S. PATENT DOCUMENTS

| | | | |
|---|---|---|---|
| 2,542,233 A * | 2/1951 | Carroll | A61F 5/445 604/337 |
| 2,544,579 A * | 3/1951 | Ardner | A61F 5/445 604/337 |
| 3,214,502 A | 10/1965 | Schaar | |
| 3,832,510 A | 8/1974 | Pfau et al. | |
| 3,915,171 A | 10/1975 | Shermeta | |
| 3,941,133 A | 3/1976 | Chen | |
| 4,231,369 A | 11/1980 | Sorensen et al. | |
| 4,372,308 A | 2/1983 | Steer et al. | |
| 4,449,970 A | 5/1984 | Bevan et al. | |
| 4,668,227 A | 5/1987 | Kay | |
| 4,754,264 A | 6/1988 | Okada et al. | |
| 4,775,374 A | 10/1988 | Cilento et al. | |
| 4,834,731 A | 5/1989 | Nowak et al. | |
| 4,973,323 A | 11/1990 | Kaczmarek et al. | |
| 4,982,742 A | 1/1991 | Claude | |
| 5,013,307 A | 5/1991 | Broida | |
| 5,016,645 A | 5/1991 | Williams et al. | |
| 5,051,259 A | 9/1991 | Olsen et al. | |
| 5,074,851 A | 12/1991 | Plass et al. | |
| 5,111,812 A | 5/1992 | Swanson et al. | |
| 5,167,650 A | 12/1992 | Johnsen et al. | |
| 5,197,895 A | 3/1993 | Stupecky | |
| 5,237,995 A | 8/1993 | Cano | |
| 5,318,543 A | 6/1994 | Ross et al. | |
| 5,358,488 A | 10/1994 | Suriyapa | |
| 5,486,158 A | 1/1996 | Samuelsen | |
| 5,570,082 A | 10/1996 | Mahgerefteh et al. | |
| 5,593,397 A | 1/1997 | La Gro | |
| 5,626,135 A | 5/1997 | Sanfilippo | |
| 5,672,163 A * | 9/1997 | Ferreira | A61F 5/441 604/333 |
| 5,677,221 A | 10/1997 | Tseng | |
| 5,704,905 A | 1/1998 | Jensen et al. | |
| 5,790,036 A | 8/1998 | Fisher et al. | |
| 5,800,415 A | 9/1998 | Olsen | |
| 5,816,252 A | 10/1998 | Faries et al. | |
| 5,834,009 A | 11/1998 | Sawers et al. | |
| 5,879,292 A | 3/1999 | Sternberg et al. | |
| 5,942,186 A | 8/1999 | Sanada et al. | |
| 6,015,399 A | 1/2000 | Mracna et al. | |
| 6,025,725 A | 2/2000 | Gershenfeld et al. | |
| 6,057,689 A | 5/2000 | Saadat | |
| 6,103,033 A | 8/2000 | Say et al. | |
| 6,135,986 A * | 10/2000 | Leisner | A61F 5/441 604/324 |
| 6,165,005 A | 12/2000 | Mills et al. | |
| 6,171,289 B1 * | 1/2001 | Millot | A61F 5/443 604/336 |
| 6,206,864 B1 | 3/2001 | Kavanagh et al. | |
| 6,246,330 B1 | 6/2001 | Nielsen | |
| 6,297,422 B1 | 10/2001 | Hansen et al. | |
| 6,407,308 B1 | 6/2002 | Roe et al. | |
| 6,433,244 B1 | 8/2002 | Roe et al. | |
| 6,482,491 B1 | 11/2002 | Samuelsen et al. | |
| 6,485,476 B1 | 11/2002 | Von et al. | |
| 6,520,943 B1 | 2/2003 | Wagner | |
| 6,659,989 B1 | 12/2003 | Otto | |
| 6,677,859 B1 | 1/2004 | Bensen | |
| 6,764,474 B2 | 7/2004 | Nielsen et al. | |
| 7,049,478 B1 | 5/2006 | Smith | |
| 7,066,919 B2 | 6/2006 | Sauerland et al. | |
| 7,150,728 B2 | 12/2006 | Hansen et al. | |
| 7,166,091 B1 * | 1/2007 | Zeltner | A61F 5/445 604/338 |
| 7,199,501 B2 | 4/2007 | Pei et al. | |
| 7,214,217 B2 | 5/2007 | Pedersen et al. | |
| 7,221,279 B2 | 5/2007 | Nielsen | |
| 7,326,190 B2 * | 2/2008 | Botten | A61F 5/441 604/332 |
| 7,341,578 B2 * | 3/2008 | Bulow | A61F 5/441 604/338 |
| 7,347,844 B2 | 3/2008 | Cline et al. | |
| 7,367,965 B2 * | 5/2008 | Poulsen | A61F 5/441 604/324 |
| 7,422,578 B2 | 9/2008 | Shan et al. | |
| 7,559,922 B2 * | 7/2009 | Botten | A61F 5/441 604/332 |
| 7,625,362 B2 * | 12/2009 | Boehringer | A61M 1/74 604/304 |
| 7,641,612 B1 | 1/2010 | McCall | |
| 7,943,812 B2 | 5/2011 | Stroebeck et al. | |
| 7,981,098 B2 * | 7/2011 | Boehringer | A61M 1/74 604/319 |
| 8,061,360 B2 | 11/2011 | Locke et al. | |
| 8,277,427 B2 | 10/2012 | Edvardsen et al. | |
| 8,319,003 B2 | 11/2012 | Olsen et al. | |
| 8,398,575 B1 | 3/2013 | McCall | |
| 8,398,603 B2 * | 3/2013 | Thirstrup | A61B 5/746 602/41 |
| 8,399,732 B2 | 3/2013 | Oelund et al. | |
| 8,409,158 B2 * | 4/2013 | Edvardsen | A61F 5/443 604/335 |
| 8,449,471 B2 | 5/2013 | Tran | |
| 8,474,338 B2 | 7/2013 | Gelman et al. | |
| 8,500,718 B2 | 8/2013 | Locke et al. | |
| 8,632,492 B2 | 1/2014 | Delegge | |
| 8,680,991 B2 | 3/2014 | Tran | |
| 8,684,982 B2 * | 4/2014 | Nguyen-DeMary | A61F 5/441 604/327 |
| 8,740,865 B2 | 6/2014 | Krystek et al. | |
| 8,795,257 B2 | 8/2014 | Coulthard et al. | |
| D712,545 S | 9/2014 | Igwebuike et al. | |
| 8,821,464 B2 | 9/2014 | Hanuka et al. | |
| 8,975,465 B2 | 3/2015 | Hong et al. | |
| 8,979,813 B2 | 3/2015 | Uveborn | |
| 9,046,085 B2 | 6/2015 | Schoess et al. | |
| 9,066,812 B2 * | 6/2015 | Edvardsen | A61F 5/443 |
| 9,216,104 B2 * | 12/2015 | Thirstrup | A61F 5/4404 |
| 9,308,332 B2 | 4/2016 | Heppe | |
| 9,322,797 B1 | 4/2016 | Lastinger et al. | |
| 9,629,779 B2 | 4/2017 | Grum-Schwensen et al. | |
| 9,629,964 B2 | 4/2017 | Wuepper | |
| 9,693,908 B2 | 7/2017 | Eriksson et al. | |
| 9,770,359 B2 | 9/2017 | Edvardsen et al. | |
| 9,788,991 B2 | 10/2017 | Bird | |
| 9,867,934 B2 | 1/2018 | Heppe | |
| 9,928,341 B2 | 3/2018 | Angelides | |
| 10,016,298 B2 * | 7/2018 | Thirstrup | A61F 13/42 |
| D826,740 S | 8/2018 | Stevens et al. | |
| 10,500,084 B2 * | 12/2019 | Hansen | A61F 5/443 |
| 10,531,977 B2 | 1/2020 | Schoess et al. | |
| 10,646,370 B2 * | 5/2020 | Keleny | A61F 5/441 |
| 10,792,184 B2 | 10/2020 | Hvid et al. | |
| 10,799,385 B2 * | 10/2020 | Hansen | G01M 3/40 |
| 10,849,781 B2 * | 12/2020 | Hansen | A61F 5/4404 |
| 10,874,541 B2 * | 12/2020 | Seres | A61B 5/002 |
| 10,987,243 B2 * | 4/2021 | Thirstrup | A61B 5/746 |
| 11,096,818 B2 * | 8/2021 | Thirstrup | A61F 13/02 |
| 11,135,084 B2 * | 10/2021 | Seres | A61B 5/14539 |
| 11,406,525 B2 * | 8/2022 | Seres | A61F 5/445 |
| 11,471,318 B2 * | 10/2022 | Hansen | A61F 5/448 |
| 11,491,042 B2 * | 11/2022 | Seres | A61B 5/14539 |
| 11,534,323 B2 * | 12/2022 | Hansen | A61F 2/64 |
| 11,540,937 B2 * | 1/2023 | Hansen | A61B 5/4283 |
| 11,547,595 B2 * | 1/2023 | Hansen | A61B 5/4851 |
| 11,547,596 B2 * | 1/2023 | Hansen | A61F 5/44 |
| 11,559,423 B2 * | 1/2023 | Speiermann | A61F 5/445 |
| 11,559,426 B2 * | 1/2023 | Sletten | A61F 5/445 |
| 11,589,811 B2 * | 2/2023 | Hansen | A61B 5/7455 |
| 11,590,015 B2 * | 2/2023 | Hansen | A61F 5/443 |
| 11,607,334 B2 * | 3/2023 | Hansen | A61F 5/44 |
| 11,612,508 B2 * | 3/2023 | Hansen | A61F 5/445 604/336 |
| 11,612,509 B2 * | 3/2023 | Hansen | A61F 5/445 604/344 |

(56) References Cited

U.S. PATENT DOCUMENTS

| | | | |
|---|---|---|---|
| 11,622,719 B2* | 4/2023 | Hansen | A61F 5/443 |
| | | | 600/301 |
| 11,628,084 B2* | 4/2023 | Hansen | A61B 5/6833 |
| | | | 604/344 |
| 11,679,021 B2* | 6/2023 | Hansen | A61F 5/445 |
| | | | 604/344 |
| 11,701,248 B2* | 7/2023 | Hansen | A61F 5/445 |
| | | | 604/318 |
| 11,730,622 B2* | 8/2023 | Hansen | A61F 5/4404 |
| | | | 604/336 |
| 11,786,392 B2* | 10/2023 | Hansen | A61F 5/445 |
| | | | 340/573.5 |
| 11,844,718 B2* | 12/2023 | Hansen | A61F 5/44 |
| 11,872,108 B2* | 1/2024 | Hansen | A61F 5/44 |
| 11,872,154 B2* | 1/2024 | Speiermann | A61B 5/150809 |
| 11,918,506 B2* | 3/2024 | Hansen | A61F 5/44 |
| 11,986,418 B2* | 5/2024 | Hansen | A61F 5/4404 |
| 11,998,473 B2* | 6/2024 | Hansen | A61F 5/443 |
| 11,998,474 B2* | 6/2024 | Svanegaard | A61F 5/445 |
| 2002/0019615 A1 | 2/2002 | Roe et al. | |
| 2003/0132763 A1 | 7/2003 | Ellenz | |
| 2003/0169032 A1 | 9/2003 | Minchole et al. | |
| 2004/0006320 A1 | 1/2004 | Buglino et al. | |
| 2004/0030305 A1 | 2/2004 | Sakamoto | |
| 2004/0036484 A1 | 2/2004 | Tamai | |
| 2004/0049145 A1 | 3/2004 | Flick | |
| 2004/0068244 A1 | 4/2004 | Salone et al. | |
| 2004/0078219 A1 | 4/2004 | Kaylor et al. | |
| 2004/0100376 A1 | 5/2004 | Lye et al. | |
| 2004/0106908 A1 | 6/2004 | Leise et al. | |
| 2004/0111072 A1 | 6/2004 | McKissick | |
| 2004/0133175 A1 | 7/2004 | Hagedorn-Olsen | |
| 2004/0171999 A1 | 9/2004 | Andersen et al. | |
| 2004/0193122 A1 | 9/2004 | Cline et al. | |
| 2004/0193123 A1 | 9/2004 | Fenton | |
| 2004/0216833 A1 | 11/2004 | Fleming et al. | |
| 2005/0054997 A1 | 3/2005 | Buglino et al. | |
| 2005/0065488 A1 | 3/2005 | Elliott | |
| 2005/0070863 A1* | 3/2005 | Bulow | A61F 5/441 |
| | | | 604/338 |
| 2005/0085779 A1* | 4/2005 | Poulsen | A61F 5/441 |
| | | | 604/332 |
| 2005/0101841 A9 | 5/2005 | Kaylor et al. | |
| 2005/0240163 A1 | 10/2005 | Andersen | |
| 2005/0261645 A1* | 11/2005 | Conrad | A61F 5/445 |
| | | | 604/332 |
| 2006/0015081 A1 | 1/2006 | Suzuki et al. | |
| 2006/0025727 A1* | 2/2006 | Boehringer | A61M 1/966 |
| | | | 604/313 |
| 2006/0052752 A1 | 3/2006 | McMichael | |
| 2006/0194324 A1 | 8/2006 | Faries et al. | |
| 2006/0271002 A1* | 11/2006 | Botten | A61F 5/441 |
| | | | 604/339 |
| 2007/0010256 A1 | 1/2007 | Klabunde et al. | |
| 2007/0035405 A1 | 2/2007 | Wada et al. | |
| 2007/0135782 A1 | 6/2007 | Bager et al. | |
| 2007/0142796 A1 | 6/2007 | Mosbacher et al. | |
| 2007/0185464 A1 | 8/2007 | Fattman et al. | |
| 2008/0038536 A1 | 2/2008 | Strobech et al. | |
| 2008/0071214 A1 | 3/2008 | Locke et al. | |
| 2008/0075934 A1 | 3/2008 | Barlow et al. | |
| 2008/0091154 A1* | 4/2008 | Botten | A61F 5/441 |
| | | | 96/155 |
| 2008/0096726 A1 | 4/2008 | Riley et al. | |
| 2008/0097360 A1 | 4/2008 | Andersen et al. | |
| 2008/0140057 A1 | 6/2008 | Wood et al. | |
| 2008/0234641 A1 | 9/2008 | Locke et al. | |
| 2008/0275327 A1* | 11/2008 | Faarbaek | A61B 5/6833 |
| | | | 600/382 |
| 2008/0278337 A1 | 11/2008 | Huang et al. | |
| 2008/0300559 A1 | 12/2008 | Gustafson et al. | |
| 2008/0306459 A1 | 12/2008 | Albrectsen | |
| 2009/0009342 A1 | 1/2009 | Karjalainen | |
| 2009/0012501 A1* | 1/2009 | Boehringer | A61M 1/966 |
| | | | 604/543 |
| 2009/0118600 A1 | 5/2009 | Ortiz et al. | |
| 2009/0118687 A1 | 5/2009 | Kristensen et al. | |
| 2009/0167286 A1 | 7/2009 | Naylor et al. | |
| 2009/0173935 A1 | 7/2009 | Cho et al. | |
| 2009/0216169 A1 | 8/2009 | Hansen et al. | |
| 2009/0227969 A1 | 9/2009 | Jaeb et al. | |
| 2009/0247970 A1* | 10/2009 | Keleny | B01D 46/0036 |
| | | | 156/247 |
| 2010/0010460 A1* | 1/2010 | Butler | A61F 5/441 |
| | | | 604/333 |
| 2010/0030167 A1* | 2/2010 | Thirstrup | A61F 5/4404 |
| | | | 340/657 |
| 2010/0036206 A1 | 2/2010 | Lorio | |
| 2010/0072271 A1 | 3/2010 | Thorstensson | |
| 2010/0076275 A1 | 3/2010 | Chu et al. | |
| 2011/0034890 A1 | 2/2011 | Stroebech et al. | |
| 2011/0077497 A1 | 3/2011 | Oster et al. | |
| 2011/0130642 A1 | 6/2011 | Jaeb et al. | |
| 2012/0013130 A1 | 1/2012 | Jung | |
| 2012/0143154 A1* | 6/2012 | Edvardsen | A61F 5/4404 |
| | | | 604/336 |
| 2012/0143155 A1* | 6/2012 | Edvardsen | A61F 5/443 |
| | | | 604/318 |
| 2012/0172673 A1 | 7/2012 | Friedman et al. | |
| 2012/0258302 A1 | 10/2012 | Mir et al. | |
| 2012/0259230 A1 | 10/2012 | Hunt et al. | |
| 2012/0283678 A1* | 11/2012 | Nguyen-DeMary | A61F 5/445 |
| | | | 604/338 |
| 2013/0018231 A1 | 1/2013 | Hong et al. | |
| 2013/0030167 A1 | 1/2013 | Wang et al. | |
| 2013/0030397 A1 | 1/2013 | Sabeti | |
| 2013/0060213 A1 | 3/2013 | Hanuka et al. | |
| 2013/0066285 A1 | 3/2013 | Locke et al. | |
| 2013/0072886 A1* | 3/2013 | Schertiger | A61F 5/445 |
| | | | 604/335 |
| 2013/0102979 A1 | 4/2013 | Coulthard et al. | |
| 2013/0138065 A1 | 5/2013 | Buus | |
| 2013/0150769 A1 | 6/2013 | Heppe | |
| 2013/0165862 A1 | 6/2013 | Griffith et al. | |
| 2013/0192604 A1* | 8/2013 | Persson | A61M 16/047 |
| | | | 128/207.16 |
| 2013/0226116 A1 | 8/2013 | Edvardsen et al. | |
| 2013/0231620 A1* | 9/2013 | Thirstrup | A61F 5/445 |
| | | | 604/344 |
| 2013/0254141 A1 | 9/2013 | Barda et al. | |
| 2013/0261575 A1 | 10/2013 | Kiyoshi | |
| 2013/0267790 A1 | 10/2013 | Pfuetzner et al. | |
| 2013/0303867 A1 | 11/2013 | Elfstrom et al. | |
| 2013/0307570 A1 | 11/2013 | Bosaeus et al. | |
| 2013/0324955 A1 | 12/2013 | Wong et al. | |
| 2014/0051946 A1 | 2/2014 | Arne et al. | |
| 2014/0133290 A1 | 5/2014 | Yokoo et al. | |
| 2014/0200538 A1 | 7/2014 | Euliano et al. | |
| 2014/0236111 A1 | 8/2014 | Casado et al. | |
| 2014/0236335 A1 | 8/2014 | Lewis et al. | |
| 2014/0275854 A1 | 9/2014 | Venkatraman et al. | |
| 2014/0276501 A1* | 9/2014 | Cisko | A61F 5/443 |
| | | | 604/355 |
| 2014/0288381 A1* | 9/2014 | Faarbaek | A61B 5/0002 |
| | | | 600/300 |
| 2014/0303574 A1 | 10/2014 | Knutson | |
| 2014/0309600 A1 | 10/2014 | Aceto et al. | |
| 2014/0323909 A1 | 10/2014 | Kim | |
| 2014/0327433 A1 | 11/2014 | Anway et al. | |
| 2014/0336493 A1 | 11/2014 | Kulach et al. | |
| 2015/0231802 A1 | 8/2015 | Quan et al. | |
| 2015/0250639 A1* | 9/2015 | Thirstrup | A61F 13/00051 |
| | | | 156/278 |
| 2015/0257923 A1* | 9/2015 | Thirstrup | A61F 13/42 |
| | | | 604/318 |
| 2015/0351690 A1 | 12/2015 | Toth et al. | |
| 2015/0374896 A1 | 12/2015 | Du et al. | |
| 2016/0015570 A1 | 1/2016 | Heinecke et al. | |
| 2016/0084869 A1 | 3/2016 | Yuen et al. | |
| 2016/0158056 A1 | 6/2016 | Davis et al. | |
| 2016/0158969 A1 | 6/2016 | McLane et al. | |

(56) References Cited

U.S. PATENT DOCUMENTS

| | | | |
|---|---|---|---|
| 2016/0166438 A1* | 6/2016 | Rovaniemi | A61B 5/00 493/320 |
| 2016/0218555 A1 | 7/2016 | Slaby et al. | |
| 2016/0235581 A1* | 8/2016 | Keleny | A61F 5/441 |
| 2016/0278990 A1 | 9/2016 | Chen | |
| 2016/0284084 A1 | 9/2016 | Gurcan et al. | |
| 2016/0305776 A1 | 10/2016 | Mrtensson et al. | |
| 2016/0310140 A1 | 10/2016 | Belson et al. | |
| 2016/0310329 A1 | 10/2016 | Patel et al. | |
| 2016/0317728 A1 | 11/2016 | Lewis et al. | |
| 2016/0361015 A1 | 12/2016 | Wang et al. | |
| 2017/0042614 A1 | 2/2017 | Salahieh et al. | |
| 2017/0050004 A1 | 2/2017 | Tilson et al. | |
| 2017/0055896 A1 | 3/2017 | Al-Ali et al. | |
| 2017/0079530 A1 | 3/2017 | Dimaio et al. | |
| 2017/0079576 A1 | 3/2017 | Stroebech et al. | |
| 2017/0112658 A1 | 4/2017 | Hosono | |
| 2017/0156920 A1 | 6/2017 | Hunt et al. | |
| 2017/0262986 A1 | 9/2017 | Xiong et al. | |
| 2017/0319073 A1 | 11/2017 | Dimaio et al. | |
| 2017/0340474 A1* | 11/2017 | Thirstrup | A61B 5/746 |
| 2017/0348137 A1 | 12/2017 | Hvid et al. | |
| 2017/0348162 A1 | 12/2017 | Arizti et al. | |
| 2017/0360592 A1 | 12/2017 | Carrubba | |
| 2017/0367654 A1 | 12/2017 | Cheng et al. | |
| 2018/0021164 A1 | 1/2018 | Fenton | |
| 2018/0021165 A1 | 1/2018 | Fenton | |
| 2018/0049667 A1 | 2/2018 | Heppe | |
| 2018/0055359 A1 | 3/2018 | Shamim et al. | |
| 2018/0078163 A1 | 3/2018 | Welch | |
| 2018/0109852 A1 | 4/2018 | Mandapaka et al. | |
| 2018/0171183 A1 | 6/2018 | Sakurai et al. | |
| 2018/0177626 A1 | 6/2018 | Israelson | |
| 2018/0250156 A1 | 9/2018 | Lam | |
| 2018/0344533 A1 | 12/2018 | Rovaniemi | |
| 2019/0099552 A1 | 4/2019 | Zhang et al. | |
| 2019/0133810 A1* | 5/2019 | Seres | A61B 5/14539 |
| 2019/0133811 A1* | 5/2019 | Seres | A61B 5/445 |
| 2019/0133812 A1* | 5/2019 | Seres | A61B 5/445 |
| 2019/0142623 A1 | 5/2019 | Schoess et al. | |
| 2019/0175386 A1* | 6/2019 | Monty | A61F 13/0266 |
| 2019/0192066 A1 | 6/2019 | Schoess et al. | |
| 2019/0192332 A1* | 6/2019 | Hansen | G08C 17/02 |
| 2019/0192333 A1* | 6/2019 | Hansen | A61F 5/4404 |
| 2019/0192334 A1* | 6/2019 | Hansen | A61F 5/445 |
| 2019/0247050 A1 | 8/2019 | Goldsmith | |
| 2019/0374163 A1* | 12/2019 | Faarbaek | A61B 5/411 |
| 2019/0374372 A1* | 12/2019 | Seres | A61B 5/445 |
| 2020/0100931 A1 | 4/2020 | Schoess et al. | |
| 2020/0188161 A1 | 6/2020 | Seres et al. | |
| 2020/0246174 A1 | 8/2020 | Hansen et al. | |
| 2020/0246175 A1 | 8/2020 | Hansen et al. | |
| 2020/0246176 A1 | 8/2020 | Hansen et al. | |
| 2020/0246177 A1 | 8/2020 | Hansen et al. | |
| 2020/0276063 A1 | 9/2020 | Munoz Herencia | |
| 2020/0297244 A1 | 9/2020 | Brownhill et al. | |
| 2020/0306074 A1* | 10/2020 | Speiermann | A61F 5/4404 |
| 2020/0330258 A1* | 10/2020 | Hansen | A61F 5/448 |
| 2020/0330260 A1* | 10/2020 | Hansen | A61B 5/4283 |
| 2020/0337880 A1* | 10/2020 | Hansen | A61F 5/443 |
| 2020/0337881 A1* | 10/2020 | Hansen | H04M 3/244 |
| 2020/0337882 A1* | 10/2020 | Hansen | A61F 5/4404 |
| 2020/0337883 A1* | 10/2020 | Hansen | A61F 5/443 |
| 2020/0375499 A1* | 12/2020 | Hansen | A61B 5/4216 |
| 2020/0375782 A1* | 12/2020 | Hansen | G01M 3/40 |
| 2020/0375783 A1* | 12/2020 | Hansen | A61F 5/4404 |
| 2020/0375784 A1* | 12/2020 | Hansen | A61F 5/443 |
| 2020/0375785 A1* | 12/2020 | Hansen | G16H 30/40 |
| 2020/0375786 A1* | 12/2020 | Hansen | A61F 5/448 |
| 2020/0383637 A1* | 12/2020 | Hansen | A61B 5/6832 |
| 2020/0383818 A1* | 12/2020 | Hansen | A61F 5/44 |
| 2020/0383819 A1* | 12/2020 | Sletten | A61F 5/44 |
| 2020/0383820 A1* | 12/2020 | Hansen | G16H 40/40 |
| 2020/0383821 A1* | 12/2020 | Hansen | A61F 5/44 |
| 2020/0390587 A1 | 12/2020 | Svanegaard et al. | |
| 2020/0390588 A1 | 12/2020 | Hansen et al. | |
| 2020/0390589 A1 | 12/2020 | Hansen et al. | |
| 2020/0395120 A1 | 12/2020 | Svanegaard et al. | |
| 2020/0395610 A1 | 12/2020 | Ono et al. | |
| 2020/0405228 A1 | 12/2020 | Svanegaard et al. | |
| 2020/0405229 A1 | 12/2020 | Svanegaard et al. | |
| 2020/0405230 A1 | 12/2020 | Svanegaard et al. | |
| 2021/0000414 A1 | 1/2021 | Svanegaard et al. | |
| 2021/0000633 A1 | 1/2021 | Hansen et al. | |
| 2021/0000634 A1 | 1/2021 | Svanegaard et al. | |
| 2021/0000635 A1* | 1/2021 | Hansen | A61F 5/443 |
| 2021/0000636 A1* | 1/2021 | Hansen | G01N 27/041 |
| 2021/0007663 A1 | 1/2021 | Svanegaard et al. | |
| 2021/0007881 A1 | 1/2021 | Svanegaard et al. | |
| 2021/0015653 A1* | 1/2021 | Hansen | A61B 5/6833 |
| 2021/0015654 A1* | 1/2021 | Hansen | A61F 5/44 |
| 2021/0022683 A1 | 1/2021 | Faarbaek et al. | |
| 2021/0038424 A1 | 2/2021 | Svanegaard et al. | |
| 2021/0059603 A1 | 3/2021 | Svanegaard et al. | |
| 2021/0085511 A1* | 3/2021 | Hansen | A61F 5/445 |
| 2021/0085512 A1* | 3/2021 | Hansen | A61B 5/4851 |
| 2021/0100533 A1 | 4/2021 | Seres et al. | |
| 2021/0128364 A1 | 5/2021 | Cole et al. | |
| 2021/0177642 A1 | 6/2021 | Andersen et al. | |
| 2021/0212855 A1 | 7/2021 | Hansen et al. | |
| 2021/0228194 A1 | 7/2021 | Mayberg | |
| 2021/0338471 A1 | 11/2021 | Nolan et al. | |
| 2021/0361464 A1* | 11/2021 | Larsen | A61F 5/443 |
| 2021/0361465 A1 | 11/2021 | Hansen et al. | |
| 2021/0361466 A1* | 11/2021 | Hansen | A61B 90/96 |
| 2021/0361467 A1 | 11/2021 | Hansen et al. | |
| 2021/0369197 A1* | 12/2021 | Hansen | A61B 5/7435 |
| 2021/0369488 A1* | 12/2021 | Hansen | A61F 5/4404 |
| 2021/0369489 A1 | 12/2021 | Hansen et al. | |
| 2021/0369490 A1* | 12/2021 | Hansen | A61F 5/4404 |
| 2021/0386368 A1 | 12/2021 | Carlsson et al. | |
| 2022/0000652 A1* | 1/2022 | Thirstrup | A61F 5/443 |
| 2022/0031495 A1* | 2/2022 | Seres | G01F 23/261 |
| 2022/0079802 A1 | 3/2022 | Hansen | |
| 2022/0079803 A1 | 3/2022 | Windeballe et al. | |
| 2022/0087851 A1 | 3/2022 | Stroebech | |
| 2022/0117771 A1 | 4/2022 | Fearn et al. | |
| 2022/0142807 A1 | 5/2022 | Tofte | |
| 2022/0192860 A1 | 6/2022 | Hansen et al. | |
| 2022/0241104 A1 | 8/2022 | Knoedler | |
| 2022/0241105 A1 | 8/2022 | Hansen et al. | |
| 2022/0265458 A1 | 8/2022 | Carlsson et al. | |
| 2022/0378602 A1* | 12/2022 | Hansen | A61F 5/4404 |
| 2023/0190509 A1* | 6/2023 | Hansen | A61F 5/443 604/336 |
| 2023/0293335 A1* | 9/2023 | Hansen | A61B 5/0002 604/344 |
| 2023/0301818 A1* | 9/2023 | Hansen | A61L 24/0031 |
| 2023/0414397 A1* | 12/2023 | Hansen | A61F 5/4404 |

FOREIGN PATENT DOCUMENTS

| | | |
|---|---|---|
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19900611 C1 | 7/2000 |
| DE | 69722993 T2 | 7/2004 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0800804 A1 | 10/1997 |
| EP | 1275357 A2 | 1/2003 |
| EP | 1188157 B1 | 12/2005 |
| EP | 2000083 A2 | 12/2008 |
| EP | 2108345 A1 | 10/2009 |
| EP | 2453851 A2 | 5/2012 |
| EP | 2489561 A2 | 8/2012 |

(56) References Cited

FOREIGN PATENT DOCUMENTS

| | | |
|---|---|---|
| EP | 2601915 A1 | 6/2013 |
| EP | 2654646 A2 | 10/2013 |
| EP | 2738960 A1 | 6/2014 |
| EP | 3064179 A1 | 9/2016 |
| EP | 3213727 A1 | 9/2017 |
| EP | 3226946 A1 | 10/2017 |
| GB | 2219679 A | 12/1989 |
| GB | 2225951 A | 6/1990 |
| GB | 2308306 A | 6/1997 |
| GB | 2343628 A | 5/2000 |
| GB | 2465742 A | 6/2010 |
| GB | 2486968 A | 7/2012 |
| GB | 2542093 A | 3/2017 |
| GB | 2561193 A | 10/2018 |
| JP | 04-074882 A | 3/1992 |
| JP | 06-152077 A | 5/1994 |
| JP | 09-010184 A | 1/1997 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2009-519751 A | 5/2009 |
| JP | 2014-033745 A | 2/2014 |
| JP | 2014-054368 A | 3/2014 |
| KR | 10-1056989 B1 | 8/2011 |
| KR | 10-2012-0003987 A | 1/2012 |
| KR | 20-0485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/133555 A2 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/007355 A2 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/076022 A2 | 6/2012 |
| WO | 2012/084987 A2 | 6/2012 |
| WO | 2013/013197 A1 | 1/2013 |
| WO | 2014/004207 A1 | 1/2014 |
| WO | 2014/086369 A1 | 6/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2016/132738 A1 | 8/2016 |
| WO | 2016/166731 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/120432 A1 | 6/2019 |
| WO | 2019/161859 A1 | 8/2019 |
| WO | 2019/161860 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

OTHER PUBLICATIONS

International Search Report and Written Opinion received for PCT Patent Application No. PCT/DK2019/050243, mailed on Nov. 25, 2019, 15 pages.

* cited by examiner

LEAKAGE DETECTION IN AN OSTOMY DEVICE

The present disclosure relates to an ostomy system, devices thereof, method of manufacturing and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
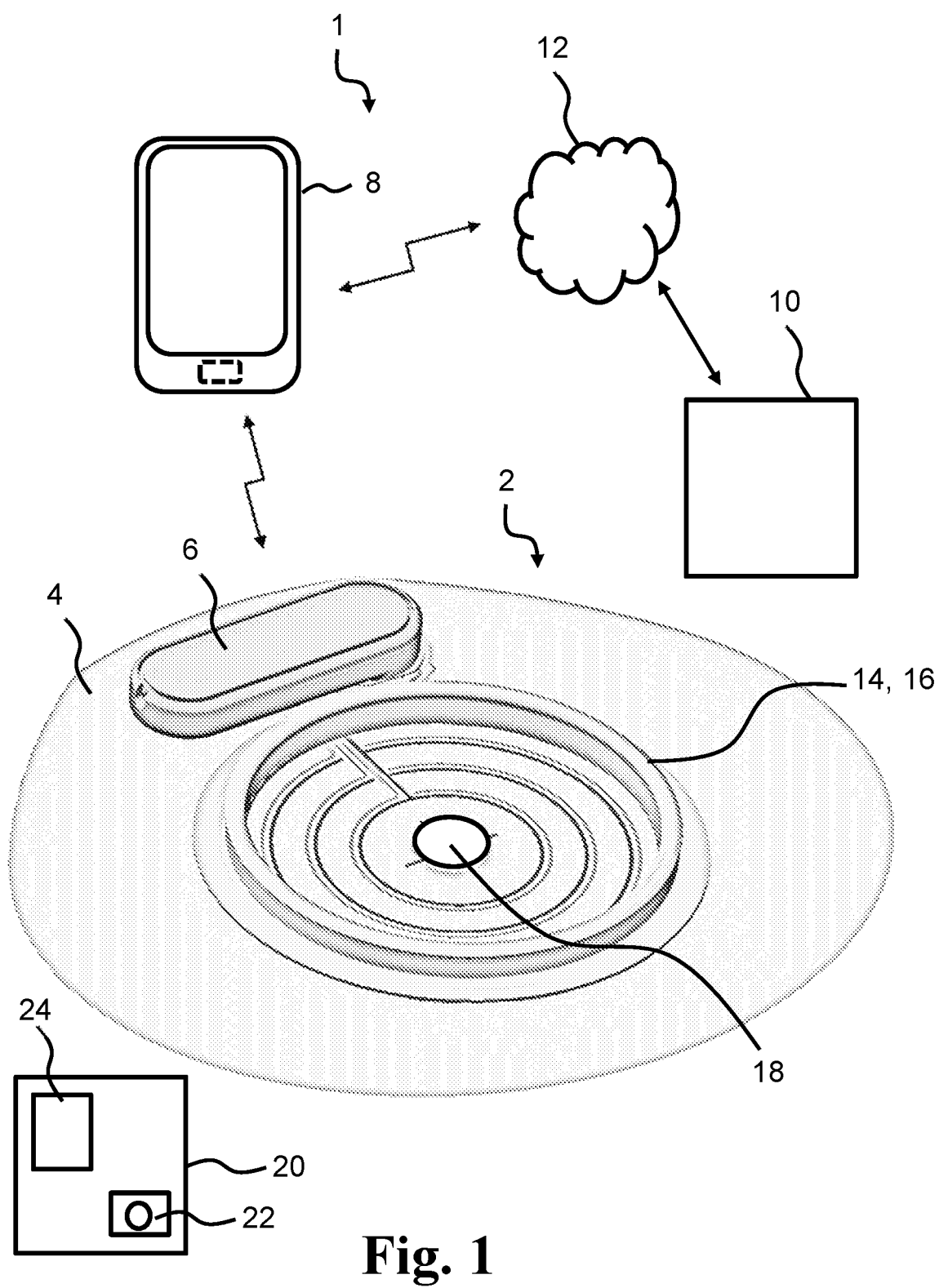
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part comprises a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a center point.

The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be a second adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyimide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate and/or the sensor assembly part on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part is configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as the electrode assembly of the base plate and/or the sensor assembly part. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate and/or the sensor assembly part may have a stomal opening, e.g. with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates or sensor assembly parts, the user forms the stomal opening during preparation of the base plate and/or the sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by $(P\_1\_1 < TH\_1\_1)$, $(P\_2\_1 > TH\_1\_2)$, and $(P\_3\_1 > TH\_1\_3)$, wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate and/or the sensor assembly part. The first threshold values ($TH\_1\_1$, $TH\_1\_2$ and $TH\_1\_3$) may be the same or different, e.g. depending on the electrode configuration of the base plate and/or the sensor assembly part. The first tertiary criterion ($P\_3\_1 < TH\_1\_3$) may be omitted in the first criteria set.

The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by $(P\_1\_1 < TH\_2\_1)$, $(P\_2\_1 < TH\_2\_2)$, and $(P\_3\_1 > TH\_2\_3)$ wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate and/or the sensor assembly part. The second threshold values ($TH\_2\_1$, $TH\_2\_2$ and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by $$(P\_1\_1 > TH\_D\_1),$$

$$(P\_2\_1 > TH\_D\_2), \text{ and}$$

$$(P\_3\_1 > TH\_D\_3)$$

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by $$(P\_1\_1 < TH\_3\_1),$$

$$(P\_2\_1 < TH\_3\_2), \text{ and}$$

$$(P\_3\_1 < TH\_3\_3)$$

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data, and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by $$(P\_4\_1 < TH\_4\_4)$$

wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal.

The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part (may alternatively be denoted a device coupling part or a monitor device coupling part) for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a base plate for an ostomy appliance, such as a base plate as described above. Also, a sensor assembly part for an ostomy appliance is disclosed, such as a sensor assembly part for being applied to a base plate. The base plate and/or the sensor assembly part may comprise: a top layer, a first adhesive layer, an electrode assembly comprising a plurality of electrodes; and a monitor interface configured for connecting the base plate and/or the sensor assembly part to a monitor device, such as mechanically connecting and/or electrically connecting the base plate and/or the sensor assembly part to a monitor device. The base plate and/or the sensor assembly part may comprise additional layers and/or features as described above.

The electrode assembly may have a first part and a second part. The first part may comprise connection parts of the plurality of electrodes. The second part may comprise sensing part of the plurality of electrodes. The electrode assembly, such as the second part of the electrode assembly, may be arranged between the first adhesive layer and the top layer.

The monitor interface may comprise a plurality of terminals electrically connected to the plurality of electrodes and configured to connect with respective terminals of the monitor device. The connection parts may form the plurality of terminals of the monitor interface.

The first adhesive layer may be provided such as to not cover a primary side of the first part of the electrode assembly. For example, the first adhesive layer may extend over a first area in a base plate plane and/or in a sensor assembly part plane, and the first part of the electrode assembly may be outside the first area.

Also disclosed is a device for connecting to a base plate and/or a sensor assembly part of an ostomy appliance, such as the above disclosed base plate. The device may be a monitor device, e.g. such as a monitor device as disclosed above. The monitor device may be configured to measure electrical parameters using electrodes of the base plate and/or sensor assembly part. The device may comprise electronic circuitry. The electronic circuitry may include a processor. The electronic circuitry may be enclosed by the device housing.

The device may comprise an appliance interface, e.g. configured for connecting the device to the base plate and/or the sensor assembly part. The appliance interface may comprise a plurality of terminals, e.g. for forming electrical connection with a plurality of electrodes of the base plate and/or the sensor assembly part. The appliance interface may comprise a device coupling part. The device coupling part may provide for coupling between the device and the base plate.

Also disclosed is a method for manufacturing a base plate or a sensor assembly part, such as a base plate or a sensor assembly part for an ostomy appliance, such as the base plate or the sensor assembly part as disclosed above.

The method may comprise: providing a top layer; providing an electrode assembly comprising a plurality of electrodes; and providing a first adhesive layer.

The electrode assembly may have a first part and a second part. The first part may comprise connection parts of the plurality of electrodes. The second part may comprise sensing part of the plurality of electrodes.

The method may further comprise assembling the top layer, the electrode assembly and the first adhesive layer, e.g. such that the electrode assembly, such as the second part of the electrode assembly, is arranged between the first adhesive layer and the top layer.

The first adhesive layer may be provided such that a primary side of the first part of the electrode assembly is not covered by the first adhesive. For example, the first adhesive layer may be provided to extend over a first area in a base plate plane and/or in a sensor assembly part plane, and the first part of the electrode assembly may be outside the first area.

By providing the first adhesive layer such that it does not cover a primary side of the first part of the electrode assembly, the first part may be accessible for connecting the electrode assembly, such as the plurality of electrodes of the electrode assembly, to connecting parts, such as terminals of a monitor device. For example, the connection parts may be accessible for the terminals of the monitor device, by the first part of the electrode assembly not being covered by the first adhesive.

The top layer, the electrode assembly and/or the first adhesive layer may be substantially planar. The top layer, the electrode assembly and/or the first adhesive layer may extend in a base plate plane and/or in a sensor assembly part plane.

A release liner may be provided on the proximal side of the first adhesive layer. The first adhesive layer may be provided with a release liner on the proximal side of the first adhesive layer. The release liner may have a distal side facing the first adhesive layer. The first adhesive layer may be provided, such as formed, on the release liner, such as on a distal side of the release liner, e.g. by scraping a thin layer of a first composition, such as a first adhesive composition, onto the release liner to form the first adhesive layer. For example, the first adhesive layer may be provided on the release liner by scraping a first composition, such as a first adhesive composition, onto the release liner. The first adhesive layer may be formed on the release liner prior to assembling the top layer, the electrode assembly and the first adhesive layer.

The release liner may be provided with one or more protrusions or elevated parts, such that upon scraping of the first composition on the distal side of the release liner, the first composition is not provided on the protruding or elevated parts. Thereby, holes, indents etc. may be provided in the first adhesive layer.

The release liner may be provided with one or more elevated parts, such as a first elevated part. The first elevated part may provide an exempt area of the release liner whereon the first composition is not disposed. The exempt area and/or the first elevated part may be aligned with the first part of the electrode assembly, e.g. after the first composition is provided on the release liner. For example, the first elevated part may prevent the first composition to be disposed on the first elevated part. Thereby, the first adhesive layer may be formed with an exempt area, i.e. an area of the release liner not covered by the first composition. The first adhesive layer and/or the release liner may be positioned such that the exempt area and/or the first elevated part of the release liner is aligned with the with the first part of the electrode assembly, such that the first adhesive layer does not cover the first part of the electrode assembly.

The electrode assembly may be provided between the top layer and the first adhesive layer. A distal side of the electrode assembly may be facing the top layer. A proximal side of the electrode assembly may be facing the first adhesive layer.

The plurality of electrodes may be provided on a proximal side of the electrode assembly.

The electrode assembly may comprise a support layer. The plurality of electrodes may be provided on the proximal side of the support layer. For example, the plurality of electrodes may be printed on the proximal side of the support layer. The plurality of electrodes may face the first adhesive layer. The plurality of electrodes may contact the first adhesive layer.

The first part of the electrode assembly may have a primary side. The first part of the electrode assembly may have a secondary side. The primary side of the first part of the electrode assembly may be a proximal side of the first part of the electrode assembly. The secondary side of the first part of the electrode assembly may be a distal side of the first part of the electrode assembly. The primary side of the first part of the electrode assembly may initially be a proximal side of the first part of the electrode assembly. The secondary side of the first part of the electrode assembly may initially be a distal side of the first part of the electrode assembly. The first part of the electrode assembly may be turned over, e.g. to expose the connection parts of the plurality of electrodes on a distal side of the base plate and/or the sensor assembly part. For example, the first part may be bend, e.g. between 170-190 degrees, such as 180 degrees, e.g. for the primary side of the first part of the electrode assembly to face distally. Thus, the primary side of the first part of the electrode assembly may, at least partly, be facing distally. For example, the first part may include a first portion arranged on a distal side of the base plate and/or the sensor assembly part, such as distal with respect to the top layer, and a second portion that extends from the second part around an edge of the top layer to the first portion.

The monitor interface may comprise a coupling part configured for forming a mechanical connection, such as a releasable coupling, between the monitor device and the base plate and/or the sensor assembly part. For example, the coupling part may be a rigid coupling part. The coupling part may allow for an electrical connection between the monitor device being coupled to the coupling part and the plurality of electrodes of the electrode assembly, such as through the plurality of terminals of the monitor interface and the monitor device.

The coupling part may be attached to the top layer, such as a distal side of the top layer. Alternatively or additionally, the coupling part may be attached to the electrode assembly, such as to a distal side of the electrode assembly, such as to a distal side of the support layer of the electrode assembly. The coupling part may be attached to the top layer and/or the electrode assembly by gluing or welding.

The coupling part may be aligned with the connection parts of the plurality of electrodes. For example, the coupling part may be positioned to cover the connection parts of the plurality of electrodes. Alternatively or additionally, the connection part of the plurality of electrodes may be positioned within a terminal interface region defined by the coupling part. The terminal interface region may be a region wherein terminals, e.g. of the base plate and/or sensor assembly part, may connect, such as mechanically and/or electrically connect, with respective terminals of a monitor device. The terminal interface region need not be a structurally delimited and/or visible region. The terminal interface region may be a region adjacent to the coupling part. Alternatively or additionally, The terminal interface region may be surrounded by the coupling part, such as a region surrounded by the coupling part. The terminal interface region may be within a 20 mm radius of the coupling part, such as within a 10 mm radius of the coupling part, such as within a 5 mm radius of the coupling part, such as within a 1 mm radius of the coupling part. The coupling part may surround the terminal interface region. The coupling part may have one or more outer sides including a first outer side. The terminal interface region may be adjacent an outer side of the coupling part, such as the first outer side.

The electrode assembly may comprise a reinforcement element. The reinforcement element may be forming at least part of the first part of the electrode assembly. The reinforcement element may provide and/or strengthen the first part of the electrode assembly, e.g. to better account for direct contact between the terminals of the monitor device and the attachment parts of the plurality of electrodes. Furthermore, the reinforcement element may facilitate bending of the first part of the electrode assembly, such as to turn the primary side of the first part of the electrode assembly to face distally.

The reinforcement element may comprise a plurality of conductive paths. The plurality of conductive paths may be connected to the plurality of electrodes, e.g. to form the connection parts of the plurality of electrodes. For example, the reinforcement element may be a flex circuit.

The base plate and/or the sensor assembly part may comprise a second adhesive layer, such as the second adhesive layer as previously disclosed. The second adhesive layer may have a proximal side and/or a distal side. The proximal side of the second adhesive layer may be facing the distal side of the electrode assembly. The distal side of the second adhesive layer may be facing the coupling part. The second adhesive layer may be between the top layer and the electrode assembly. The method may comprise providing the second adhesive layer. The method may comprise positioning the second adhesive layer, e.g. with a proximal side facing the distal side of the electrode assembly. The second adhesive layer may be provided, such as formed, on the proximal side of the top layer, e.g. such that the distal side of the second adhesive layer is facing the proximal side of the top layer. The distal side of the second adhesive layer may be facing the proximal side of the top layer. The second adhesive layer may be provided on the top layer by scraping a thin layer of a second composition, such as a second adhesive composition, onto the top layer, such as on the proximal side of the top layer, to form the second adhesive layer.

The second adhesive layer may extend over a larger area in the base plate plane and/or the sensor assembly part plane than the first adhesive layer. For example, the second adhesive layer may extend over a second area in the base plate plane and/or the sensor assembly part plane, e.g. being larger than the first area and/or covering the first area, where the first adhesive layer extends over the first area.

The base plate and/or the sensor assembly part may be cut from assembled layers, e.g. comprising the top layer, the electrode assembly, the first adhesive layer and/or the second adhesive layer. The method may comprise cutting out, such as stamping out, the base plate and/or the sensor assembly part from the assembled top layer, electrode assembly, first adhesive layer and/or second adhesive layer. The cutting out may provide a contour of the base plate and/or the sensor assembly part. The cutting out may be provided before turning over the first part of the electrode assembly. The first part of the electrode assembly may have two substantially parallel sides, e.g. in the base plate plane. The base plate may be cut from the assembled layers to provide the first part of the electrode assembly with substantially parallel sides.

The base plate and/or the sensor assembly part may comprise a stomal opening with a center point. For example, the top layer, the second adhesive, the electrode assembly, the first adhesive and/or the release liner may comprise a stomal opening with a center point, e.g. collectively forming the stomal opening with the center point of the base plate and/or the sensor assembly part.

A horizontal axis in the base plate plane and/or the sensor assembly plane may cross the center point, e.g. of the stomal opening. The horizontal axis may be orientated substantially horizontal, e.g. parallel with the ground, when the base plate is worn as intended. An upper half of the base plate may be defined as the part of the base plate in the base plate plane above the horizontal axis when the base plate is worn as intended. A lower half of the base plate may be defined as the part of the base plate in the base plate plane below the horizontal axis when the base plate is worn as intended.

The coupling part and/or the first part of the electrode assembly may be positioned on the upper half of the base plate and/or sensor assembly part. The coupling part and/or the first part of the electrode assembly may be positioned on the upper half of the base plate and/or sensor assembly part within an angular space from the horizontal axis, e.g. with respect to the center point of the base plate, from 45-135 degrees, such as from 45-90 degrees, or from 90-135 degrees. Such positioning of the coupling part and/or the first part of the electrode assembly may provide that a device, such as the monitor device, may be coupled to the coupling part and/or the first part of the electrode assembly with little or no interference with the ostomy bag. Furthermore, it may ease attachment of the device to the base plate.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown)

to the base plate (two-part ostomy appliance). The base plate has a stoma-receiving opening 18 with a stoma center point. The size and/or shape of the stomal opening 18 is typically adjusted by the user or nurse before application of the ostomy appliance to accommodate the user's stoma.

Figure 2:
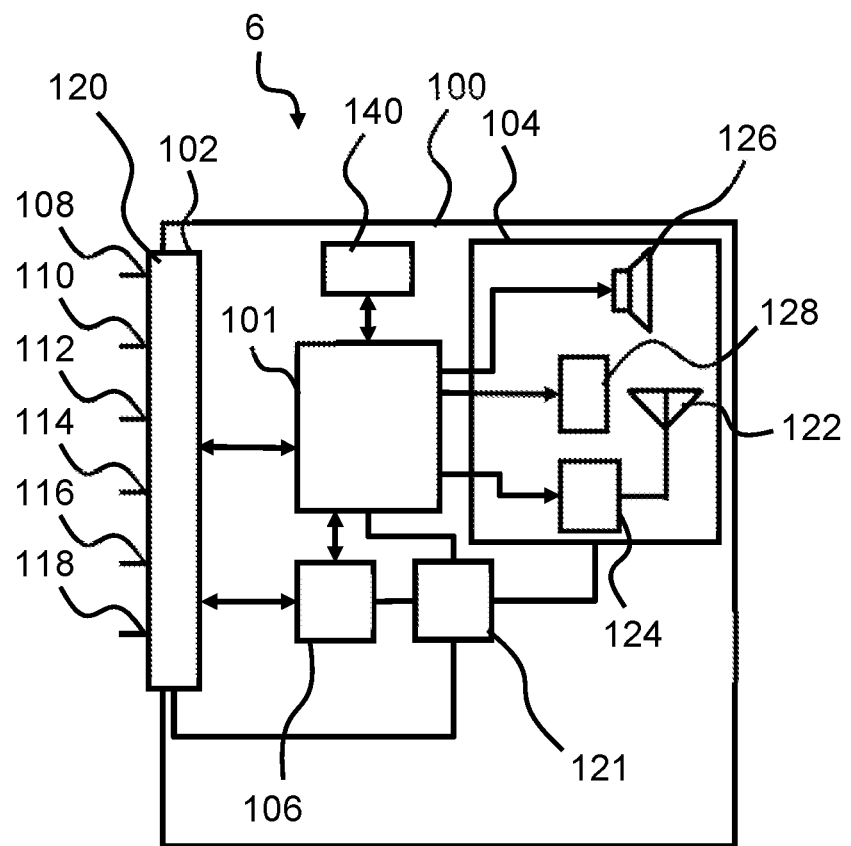
FIG. 2 illustrates an exemplary monitor device of the ostomy system.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes, FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
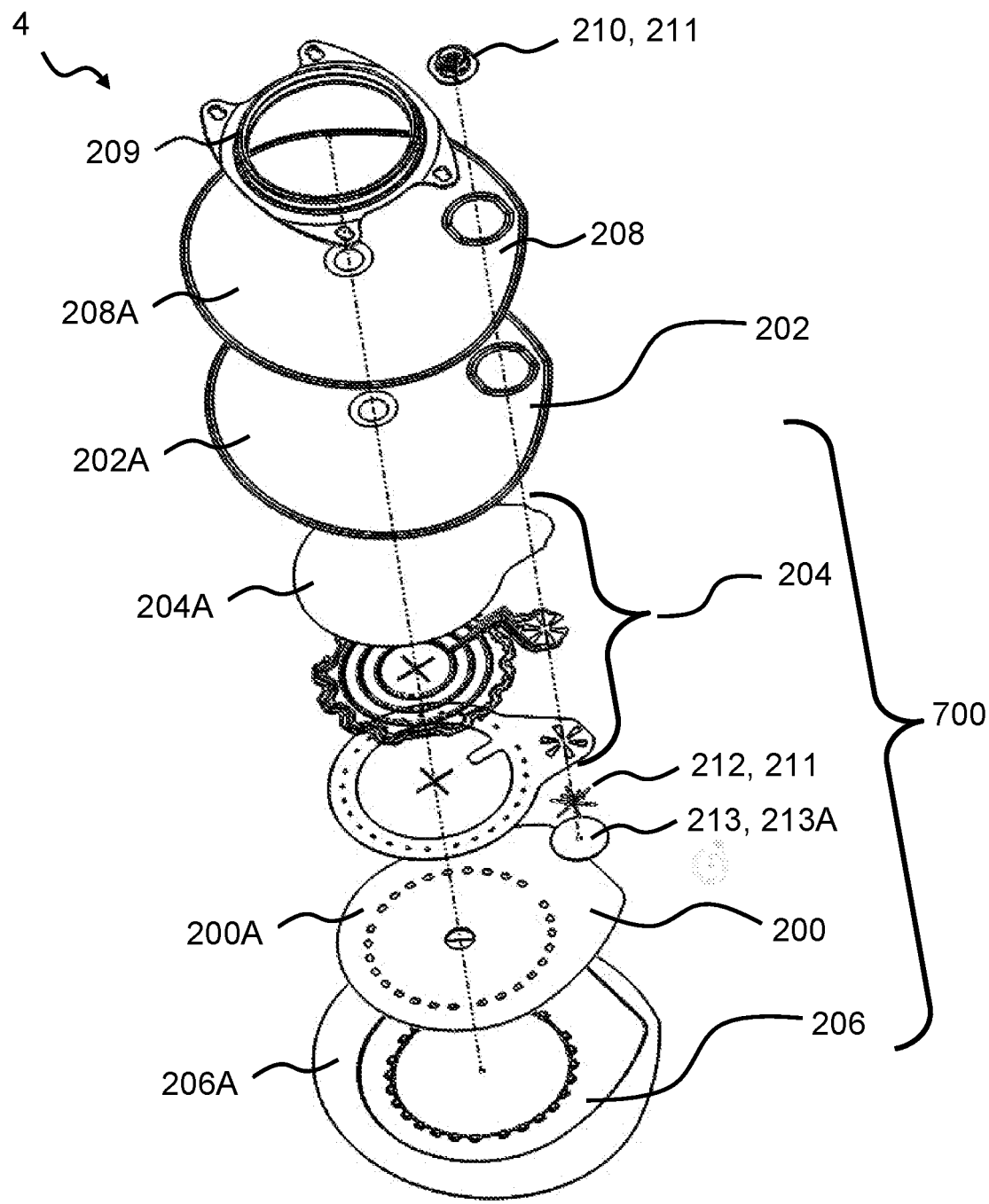
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
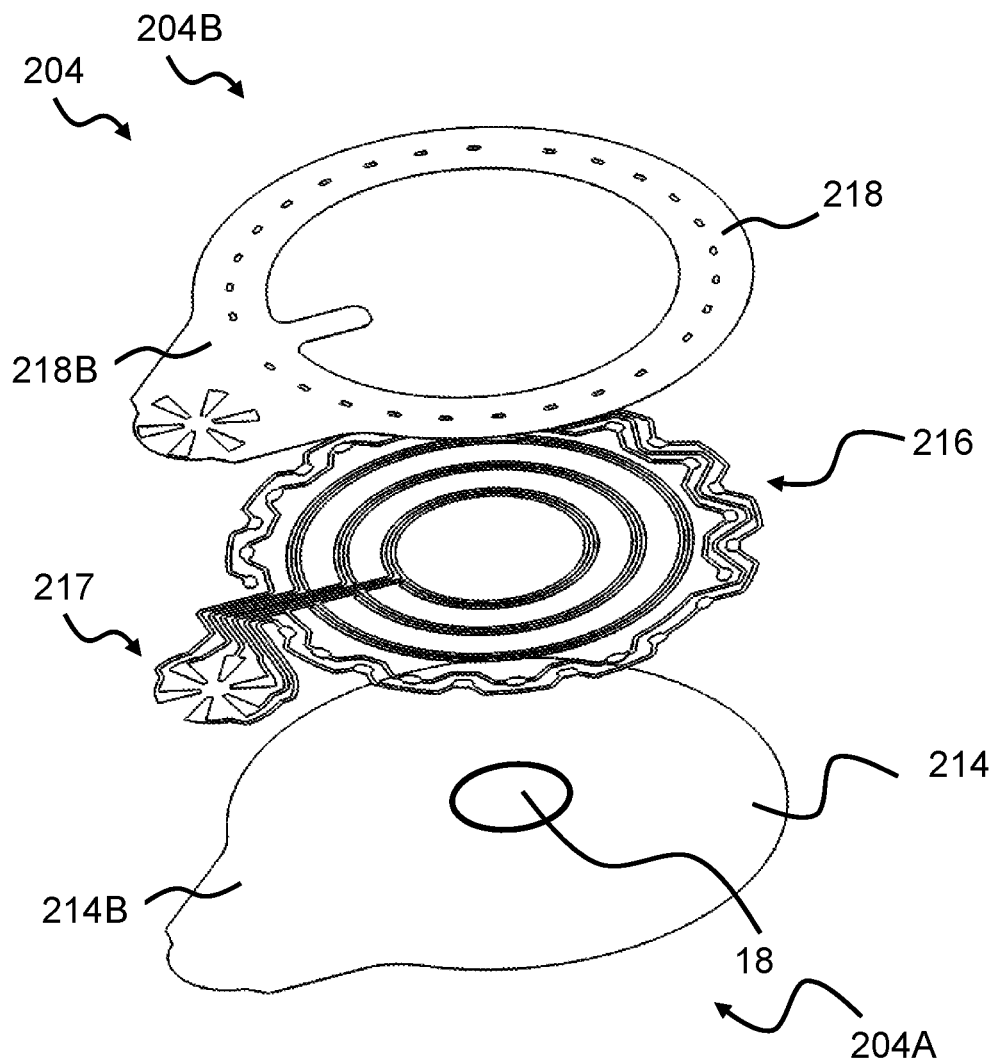
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly comprises a support layer 214 with proximal surface 214B and electrodes 216 including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are provided, such as formed, on a proximal side 214B of the support layer 214, e.g. the electrodes 216 may be positioned on the proximal side 214B of the support layer. Further, electrode assembly 204 comprises a masking element 218 with proximal surface 218B and configured to insulate electrode parts of electrodes 216 from the first adhesive layer of the base plate and/or a sensor assembly part. The masking element 218 covers or overlap with parts of the electrodes 216 when seen in the axial direction.

Figure 5:
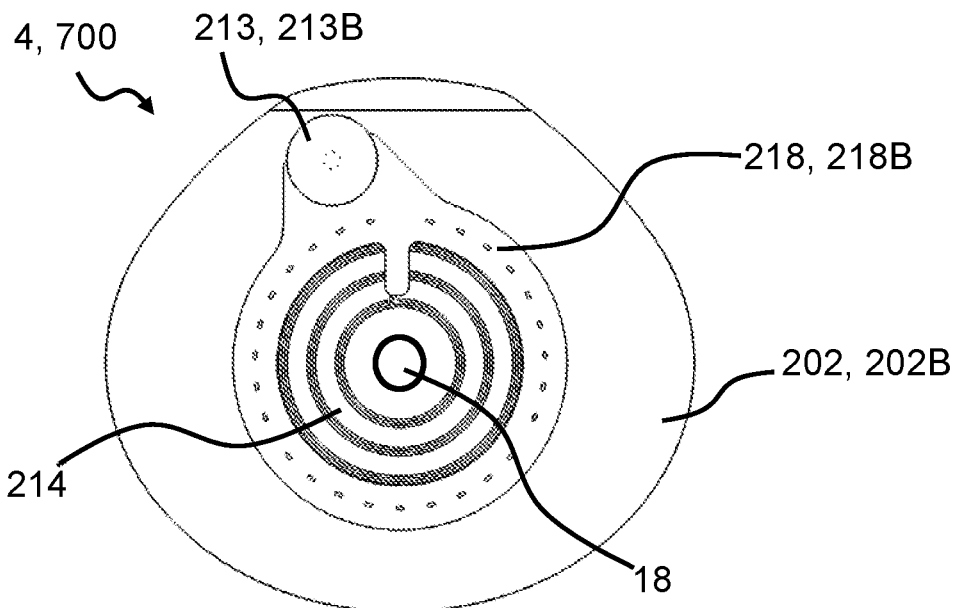
FIG. 5 is a proximal view of parts of a base plate and/or a sensor assembly part.

FIG. 5 is a proximal view of proximal surfaces of base plate parts of the base plate 4 and/or a sensor assembly part 700 without the first adhesive layer and the release liner. The base plate 4 and/or a sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or a sensor assembly part.

Figure 6:
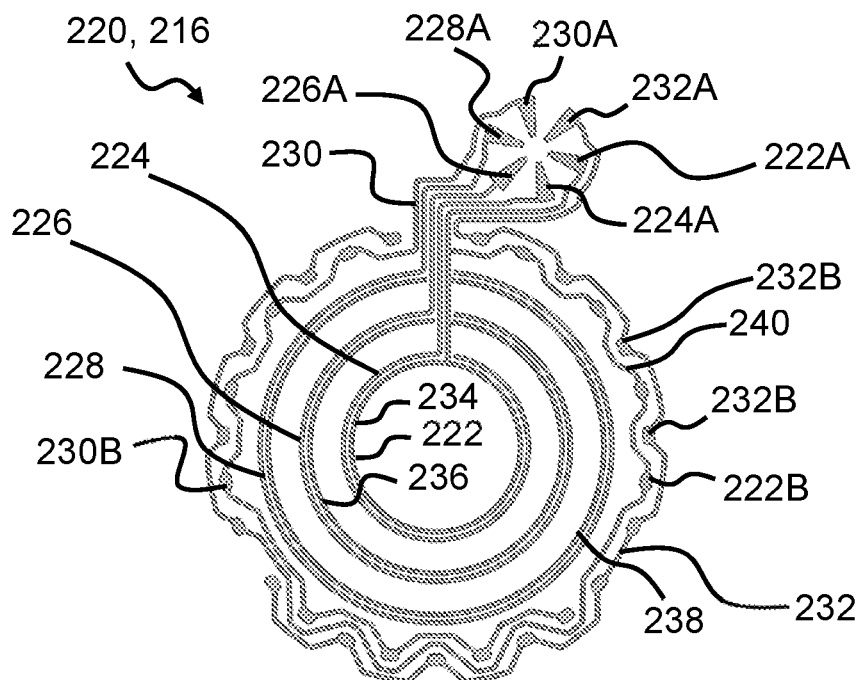
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
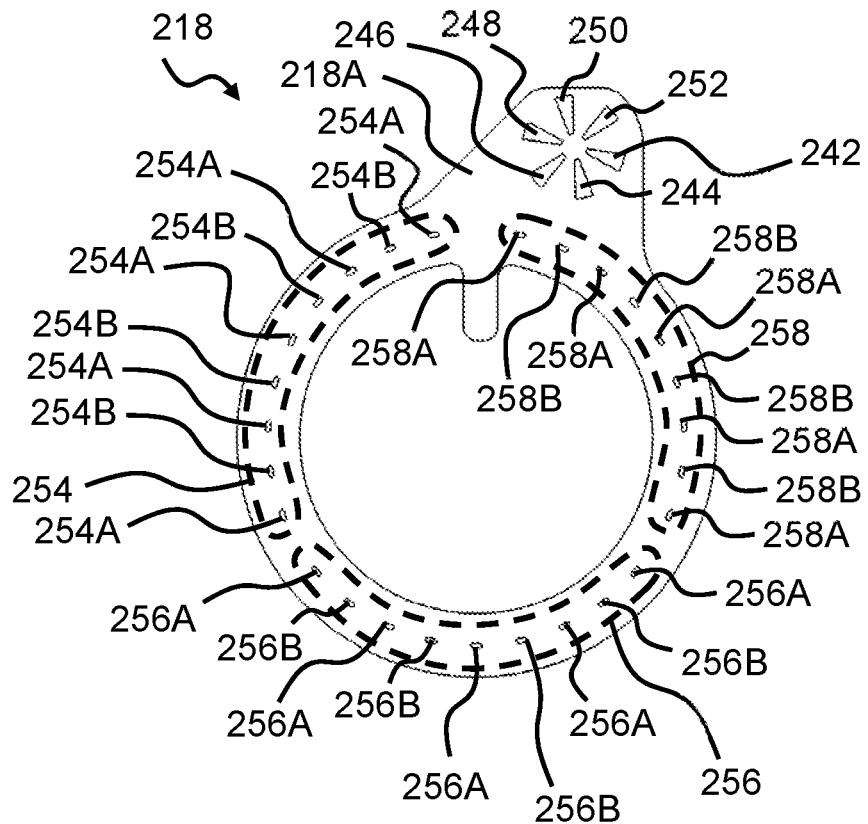
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
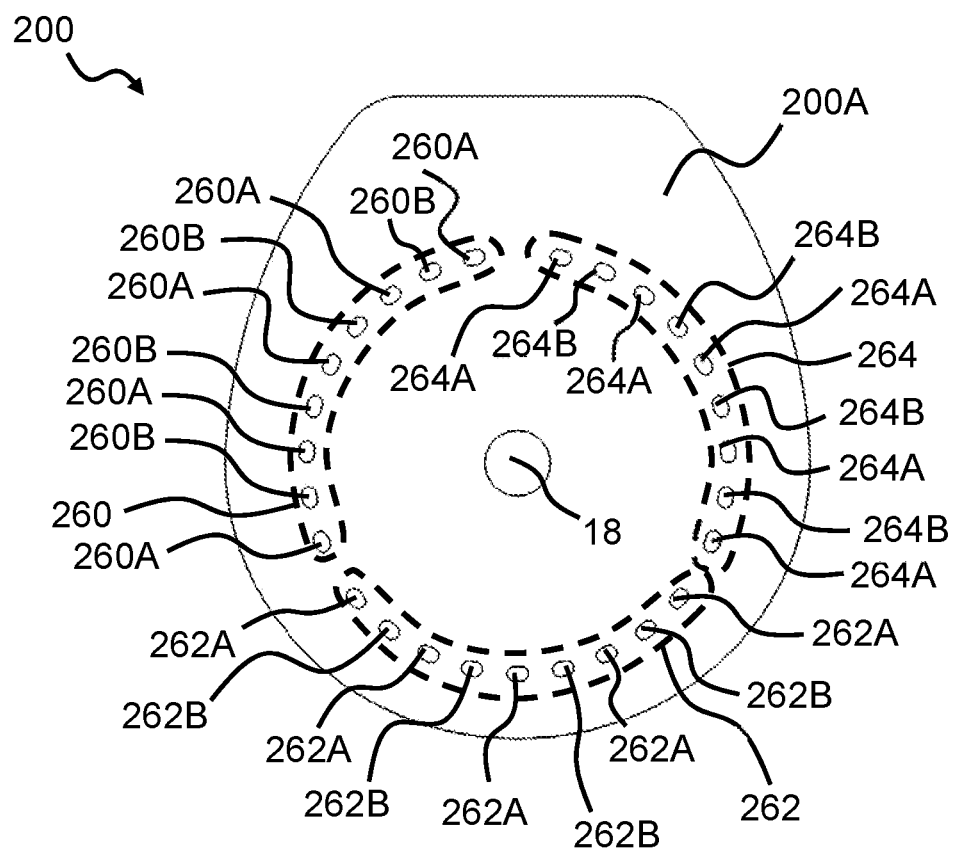
FIG. 8 is a distal view of an exemplary first adhesive layer.
Figure 9:
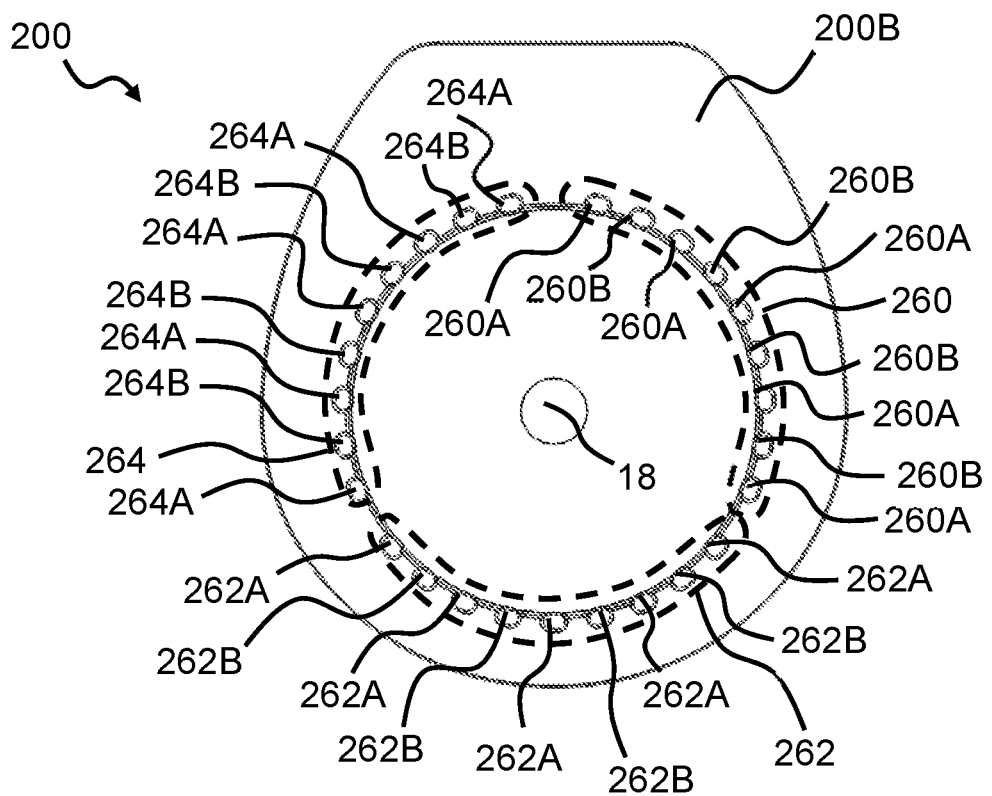
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
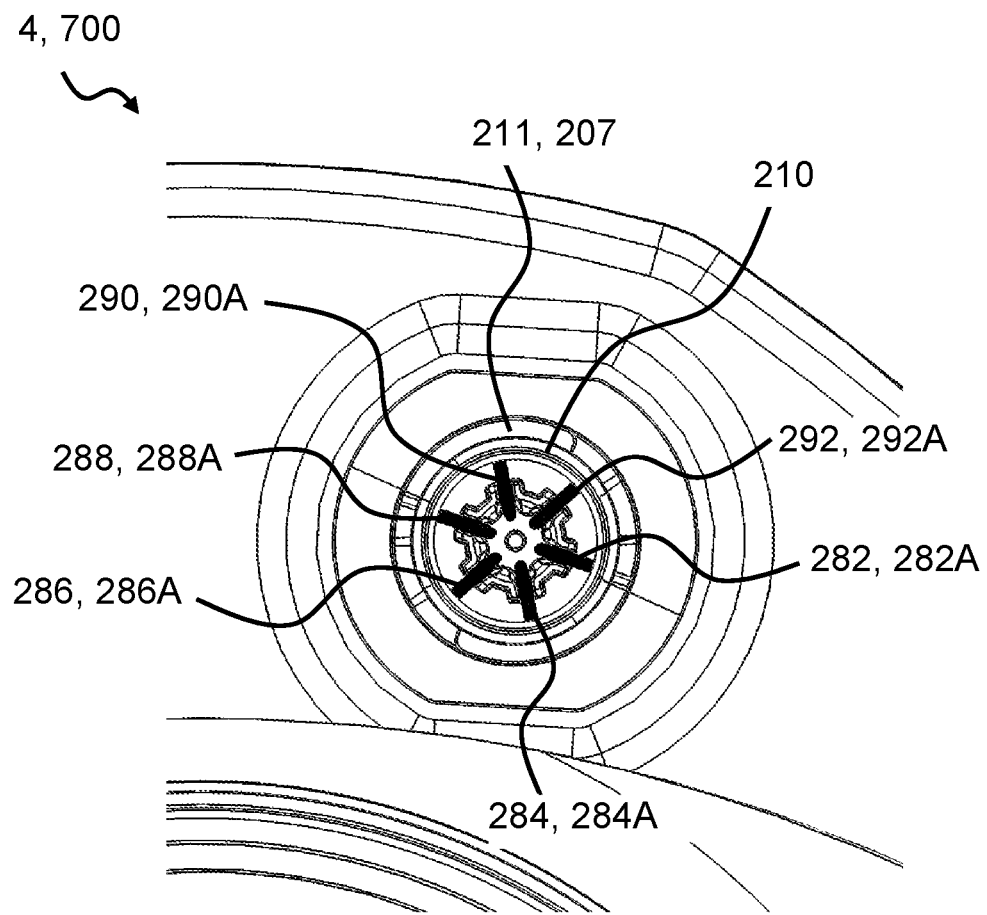
FIG. 10 is a distal view of a part of the base plate and/or a sensor assembly part including a monitor interface.

FIG. 10 is a more detailed distal view of a part of the base plate 4 and/or the sensor assembly part 700. The base plate 4 and/or the sensor assembly part 700 comprises a monitor interface 207. The monitor interface 207 comprises the first connector 211. The first connector 211 comprises coupling part 210 configured to releasably couple the monitor device to the base plate 4 and/or the sensor assembly part 700 and thus forming a releasable coupling. The first connector 211 of the monitor interface 207 comprises a plurality of terminals formed by respective terminal elements for forming respective electrical connections with respective terminals of the monitor device.

The plurality of terminals of the first connector 211 of the monitor interface 207 comprises a ground terminal element 282 forming a ground terminal 282A, a first terminal element 284 forming a first terminal 284, a second terminal element 286 forming a second terminal 286A, and a third terminal element 288 forming a third terminal 288A. The monitor interface 207 optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

Figure 11:
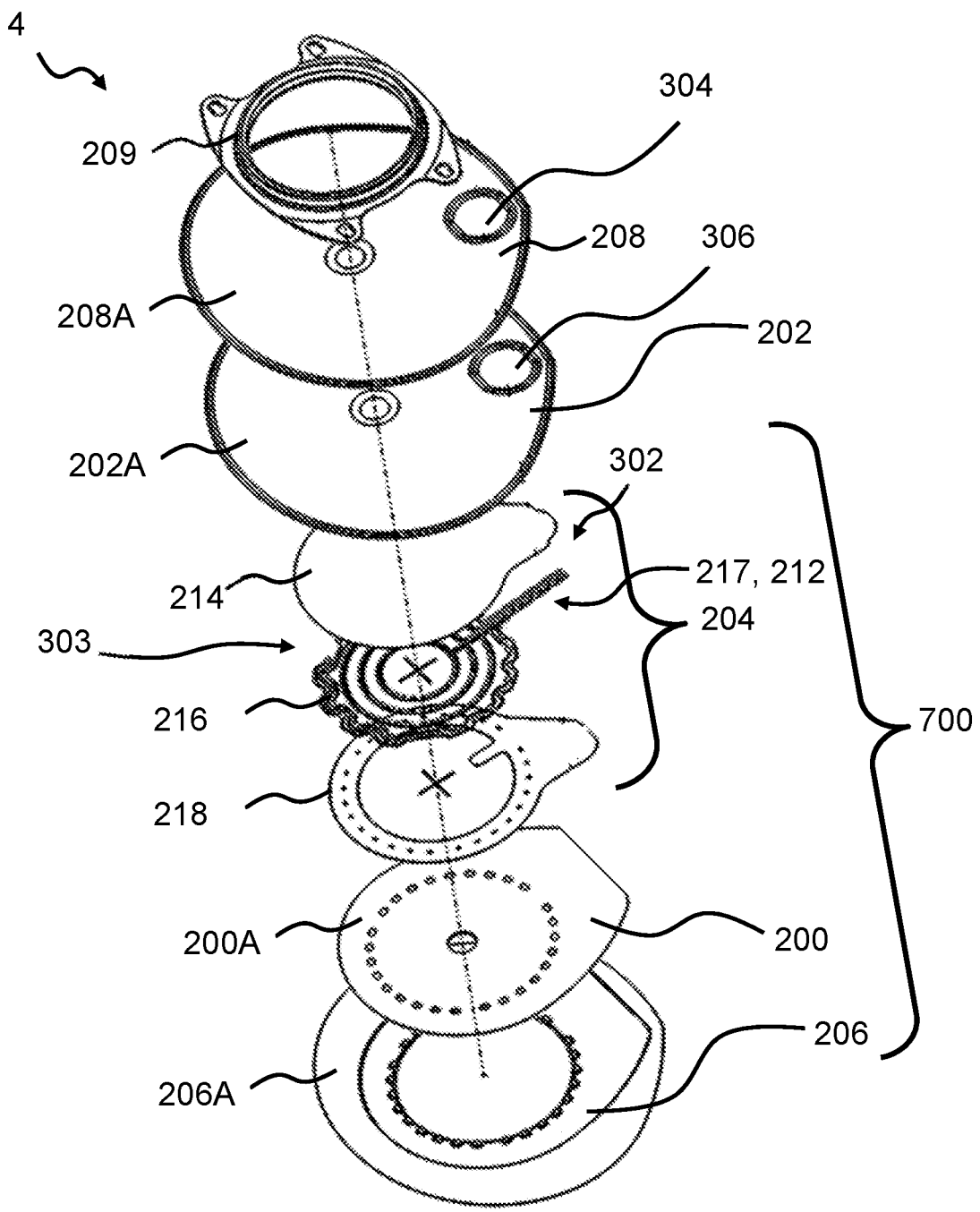
FIG. 11 illustrates an exploded view of an exemplary base plate.

FIG. 11 illustrates an exploded view of an exemplary base plate 4 of an ostomy appliance. The base plate 4 comprises a first adhesive layer 200. The base plate 4 optionally comprises a second adhesive layer 202, also denoted rim adhesive layer. The base plate 4 comprises a plurality of electrodes 216 arranged in an electrode assembly 204. The electrode assembly 204 is arranged between the first adhesive layer 200 and the second adhesive layer 202. The electrode assembly 204 optionally comprises a support layer 214. The electrodes may be formed on a proximal side of the support layer 214, such as by printing of conductive ink on the proximal side of the support layer 214. The electrode assembly 204 optionally comprises a masking element 218, e.g. covering or overlapping with parts of the electrodes 216 when seen in the axial direction, e.g. from a proximal side of the electrodes. The electrode assembly has a first part 302 comprising connection parts 217 of the plurality of electrodes 216. The electrode assembly has a second part 303. The second part 303 comprises sensing parts of the plurality of electrodes 216. The base plate 4 comprises a release liner 206. The base plate 4 comprises a top layer 208. The base plate 4 optionally comprises a coupling ring 209 for coupling an ostomy pouch to the base plate 4. Alternatively, e.g. for a one-part ostomy appliance, an ostomy pouch may be directly fastened to the base plate 4.

The base plate 4 comprises a monitor interface configured for connecting, such as mechanically and/or electronically connecting, the base plate to a monitor device. The monitor interface comprises a plurality of terminals 212 configured to form electrical connections with respective terminals of the monitor device. For example, as illustrated, the connection parts 217 may form the plurality of terminals 212 of the monitor interface. Alternatively, e.g. as shown in FIG. 3, terminal elements may be provided to form the plurality of terminals.

As illustrated by the dashed line, the layers are aligned such that the first adhesive layer 200 is not covering a primary side, such as a distal side, of the first part 302 of the electrode assembly 204.

The release liner 206 comprises a first elevated part 314 and a plurality of protrusions 316. The first adhesive layer 200 may be provided by scraping a layer of a first composition, such as a first adhesive composition, onto the release liner 206. The increased height of the protrusions 316 and elevated part(s) 314 minimizes the distance between the scraping apparatus and the release liner 206 such that the first composition is not deposited in these areas. Thereby, the protrusions 316 accounts for the sensor point openings (e.g. sensor point openings 260, 262, 264 of FIG. 8) of the first adhesive layer 200, and the first elevated part 314 accounts for the first part 302, such as the primary side of the first part 302, of the electrode assembly not being covered by the first adhesive layer 200.

Furthermore, the first adhesive layer 200 may typically show viscous properties, and the release liner 206 having the protrusions 316 and the first elevated part 314 provides that shape of the first adhesive layer 200, including the sensor point openings, is maintained while the release liner 206 is maintained.

The optional masking element 218 may be provided to insulate the plurality of electrodes 216, or parts of the plurality of electrodes 216. The masking element 218 has a plurality of terminal openings 318 to allow connection to the connecting parts 217 of the plurality of electrodes 216, e.g. from a proximal side of the electrode assembly 204.

As described in respect to FIG. 3, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for connection between the plurality of electrodes 216 of the electrode assembly 204 and terminals of a monitor device being coupled to the base plate 4.

Figure 12:
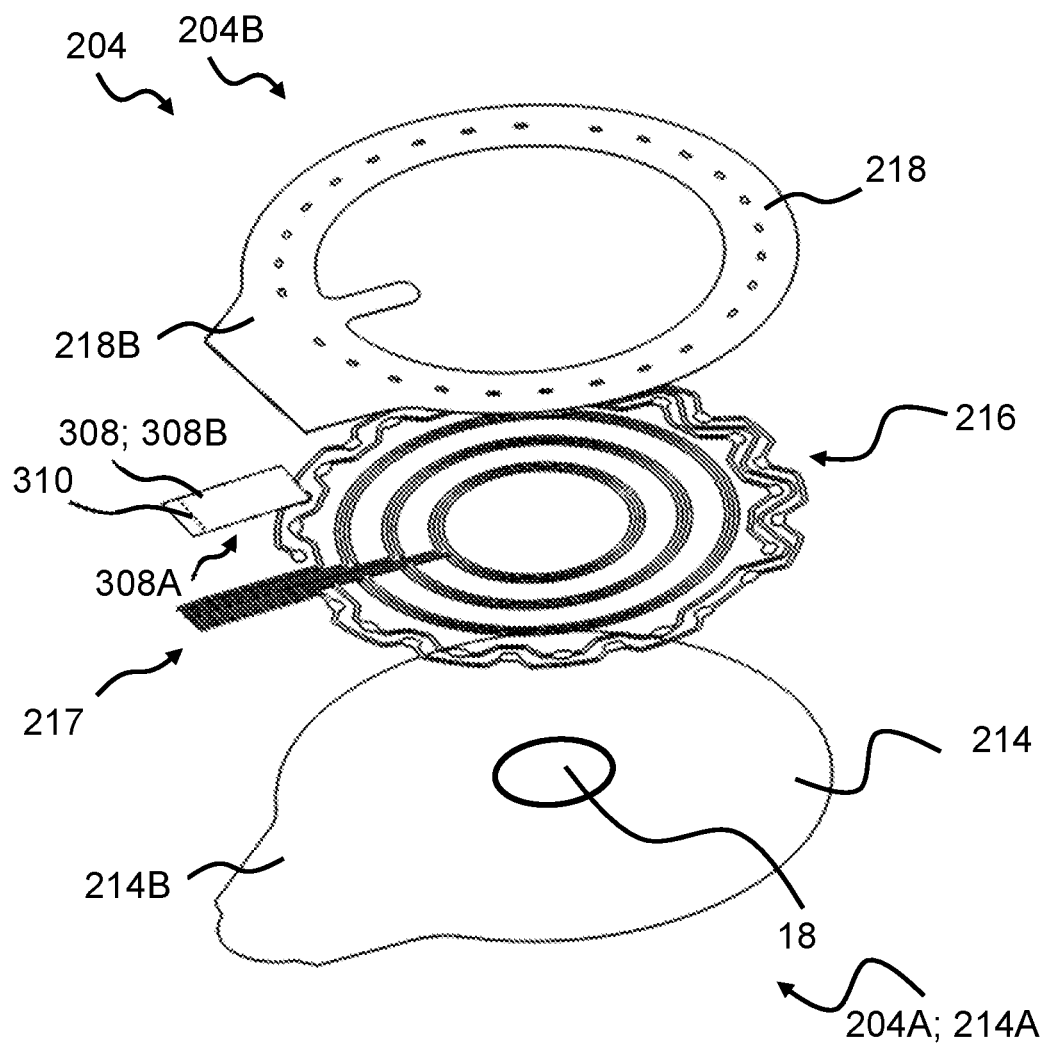
FIG. 12 illustrates an exploded view of an exemplary electrode assembly.

FIG. 12 illustrates an exploded view of an exemplary electrode assembly 204 of a base plate and/or a sensor assembly part, such as the base plate 4 or sensor assembly part 700 of FIG. 11. The electrode assembly 204 has a distal side 204A and a proximal side 204B. The electrode assembly comprises a support layer 214 with a proximal side 214B and a distal side 214A. The electrode assembly 204 comprises a plurality of electrodes 216. Each electrode of the plurality of electrodes 216 has a respective connection part 217 for connecting the electrodes 216 to respective terminal elements of the monitor interface. The electrodes 216 are provided, such as formed, on the proximal side 214B of the support layer 214, e.g. the electrodes 216 may be positioned on the proximal side 214B of the support layer 214. Further, electrode assembly 204 optionally comprises a masking element 218 with proximal side 218B and configured to insulate electrode parts of electrodes 216 from the first adhesive layer 200 of the base plate 4 and/or the sensor assembly part 700 (see FIG. 11). The masking element 218 covers or overlap with parts of the electrodes 216 when seen in the axial direction, e.g. from the proximal side 204B. The masking element 218 may be configured not to cover or overlap the connecting parts 217 of the plurality of electrodes.

In some exemplary electrode assembly 204, such as the electrode assembly 204 of FIG. 12, the electrode assembly 204 comprises a reinforcement element 308. The reinforcement element 308 may be positioned proximal to the electrode assembly 216, such as proximal to the plurality of electrodes 216, such as proximal to the plurality of connection parts 217 of the plurality of electrodes 216. The reinforcement element 308 may form at least part of a first part of the electrode assembly 204. The reinforcement element 308 may be provided with openings 310 to provide conductive pathways between sides of the reinforcement element 308, such as between a proximal side 308B and a distal side 308A of the reinforcement element 308.

Figure 13:
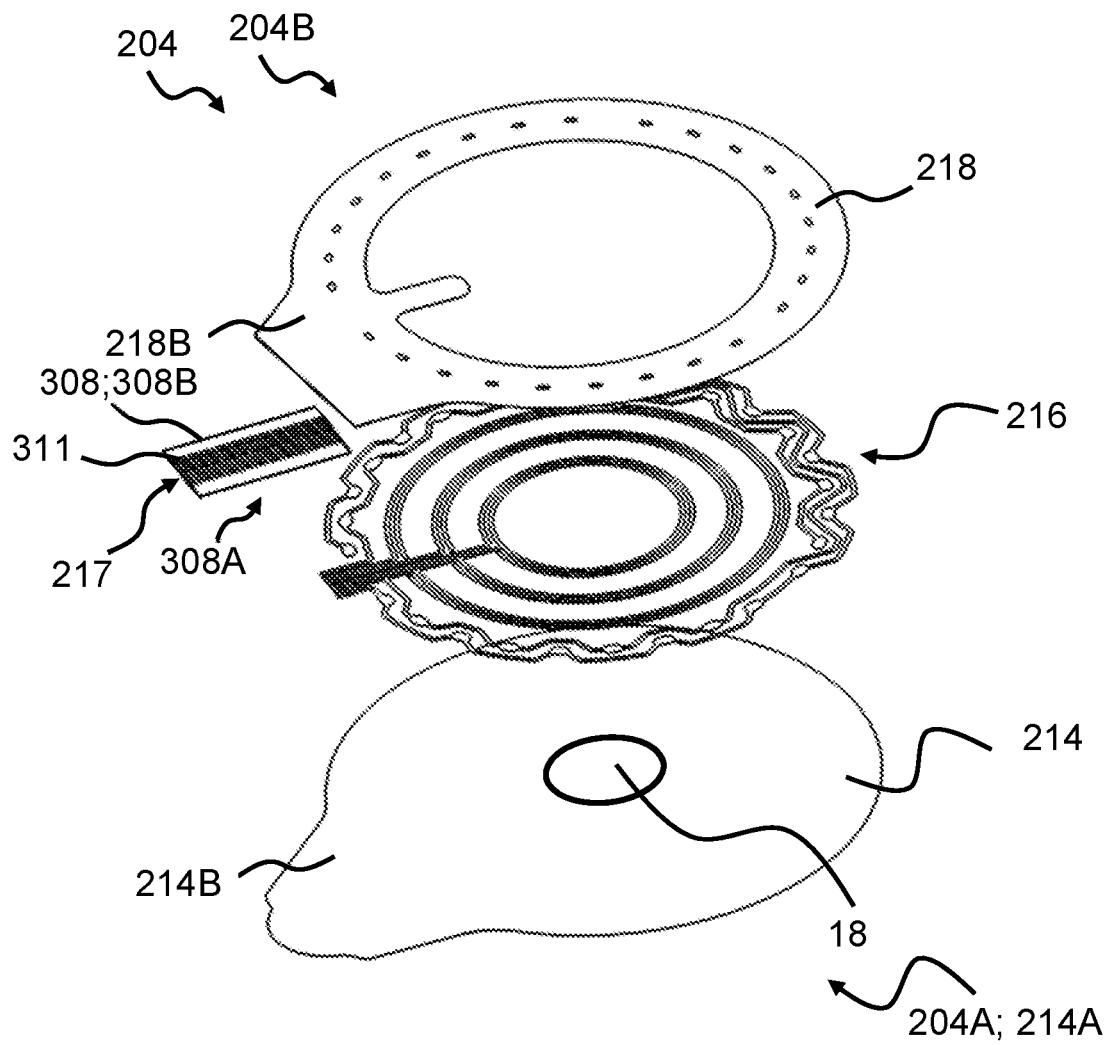
FIG. 13 illustrates an exploded view of an exemplary electrode assembly.

FIG. 13 shows an alternative to FIG. 12, wherein the reinforcement element 308 comprises a plurality of conductive paths 311. For example, the reinforcement element 308 may be a flex circuit. The plurality of conductive paths 311 may be connected to the plurality of electrodes 216. The plurality of conducive paths 311 thereby may form the connection parts 217 of the plurality of electrodes 216. The plurality of conductive paths 311 may provide conductive pathways between the proximal side 308B and the distal side 308A of the reinforcement element 308.

Figure 14:
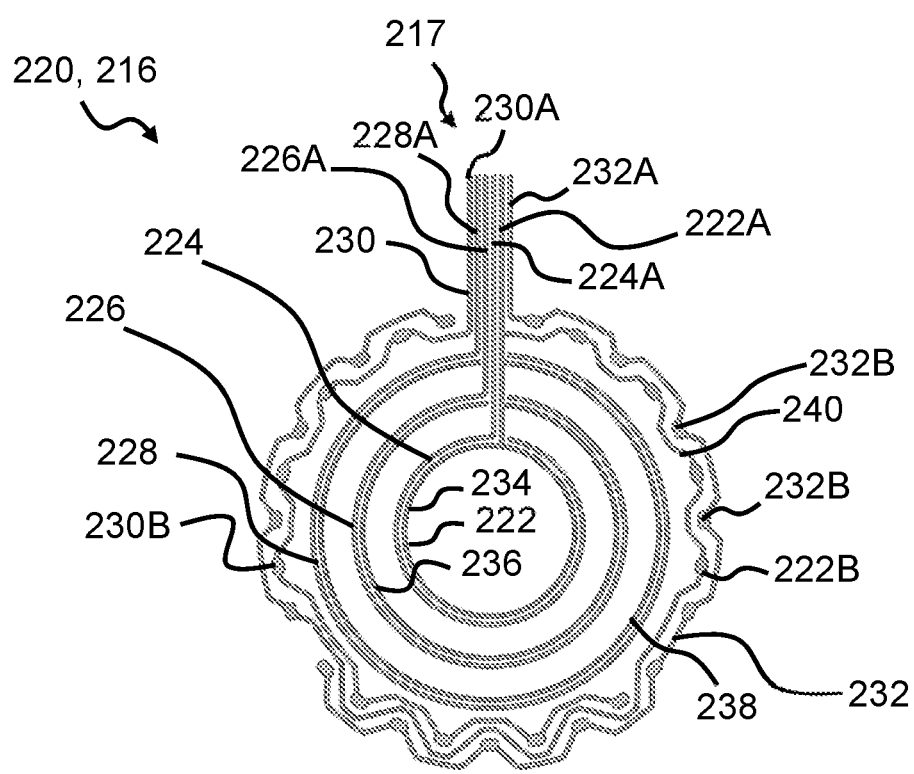
FIG. 14 shows an exemplary electrode configuration.

FIG. 14 shows an exemplary electrode configuration 220 of the plurality of electrodes 216, like the electrode configuration 220 as shown in FIG. 6, with the difference that the connection parts 217, such as the ground connection part 222A, the first connection part 224A, the second connection part 226A, the third connection part 228A, the fourth connection part 230A and/or the fifth connection part 232A, are straight connector parts.

Figure 15:
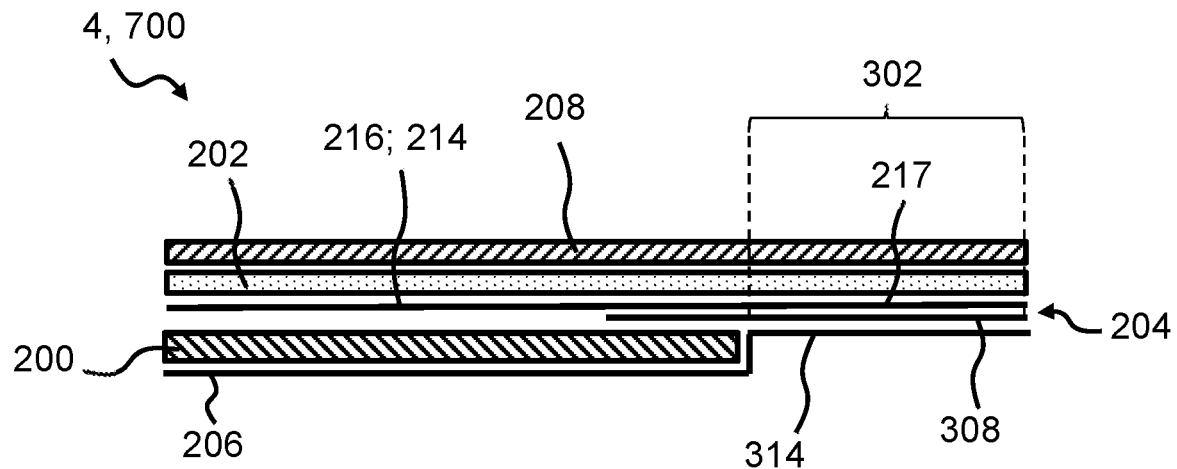
FIG. 15 shows a schematic representation of part of a base plate and/or a sensor assembly part.

FIG. 15, shows a sectional schematic representation of part of a base plate 4 and/or a sensor assembly part 700. The base plate 4 and/or the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer 200 and the second adhesive layer 202 and/or the top layer 208. The electrode assembly 204 further comprises an optional reinforcement element 308 and an optional release liner 206.

The first adhesive layer 200 is provided such that it does not cover a primary side of a first part 302 of the electrode assembly 204. For example, the release liner 206 comprises a first elevated part 314 such as to facilitate the formation of the first adhesive layer 202 to not cover the primary side of the first part 302 of the electrode assembly 204. The primary side of the first part 302 may be a proximal side of the first part 302. The first part 302 includes the connection parts of the plurality of electrodes 216 and the reinforcement element 308 or part of the reinforcement element 308. The first part 302 may include part of the support layer 214.

Figure 16:
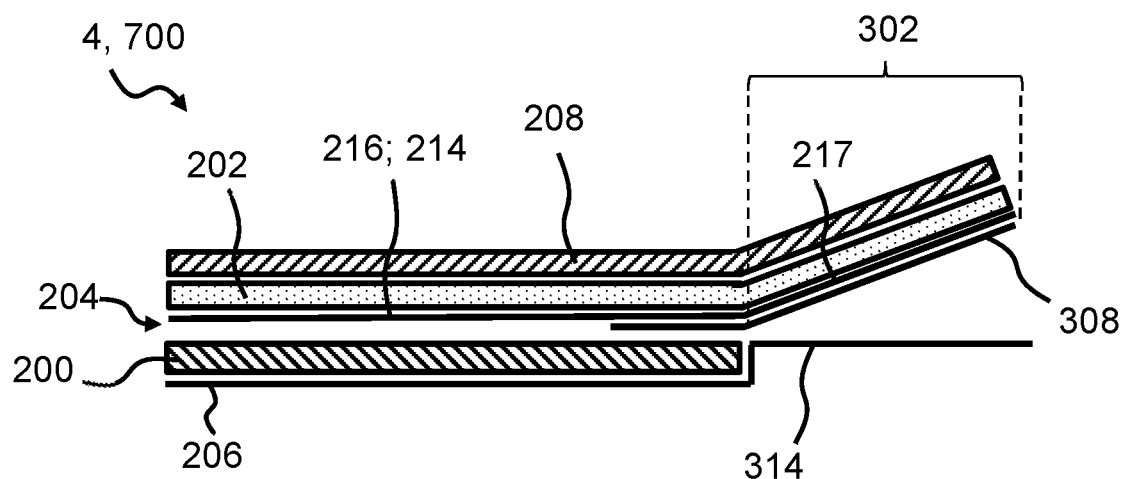
FIG. 16 shows a schematic representation of part of a base plate and/or a sensor assembly part.

FIG. 16, shows a sectional schematic representation of part of a base plate 4 and/or a sensor assembly part 700 as shown in FIG. 15, further illustrating that the connection parts 217 may be accessible, e.g. by slightly bending the first part 302 of the electrode assembly 204 in a distal direction. Alternatively, the release liner 206 may be removed so the first part 302 of the electrode assembly 204 is accessible from a proximal side.

Because the first adhesive layer 200 is not covering the first part 302 of the electrode assembly 204, the first part 302 is not adhered to the release liner or any other proximally positioned layers. Therefore, the connection parts 217 may be accessible, e.g. for connection with a monitor device. Connection to the connection parts 217 of the plurality of electrodes 216 may be provided through the reinforcement element 308, or the connection parts 217 may be formed by conductive paths of the reinforcement element 308.

Figure 17:
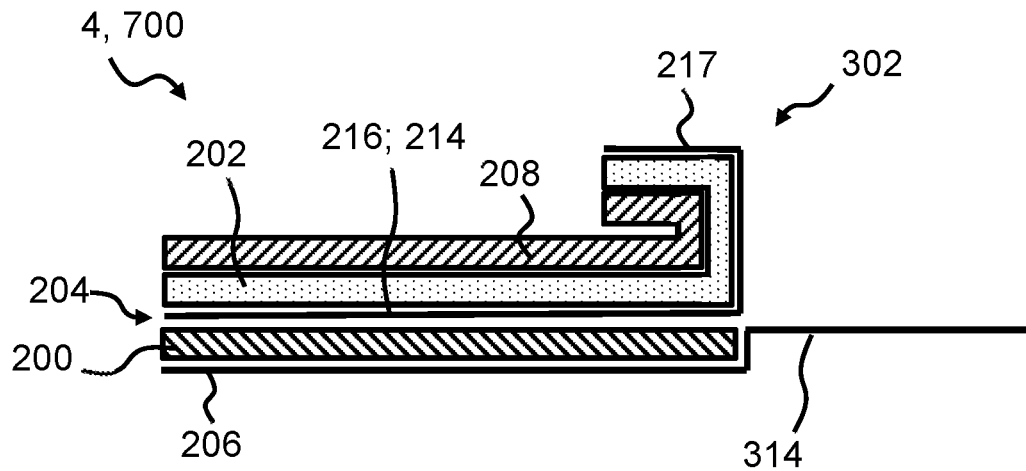
FIG. 17 shows a schematic representation of part of a base plate and/or a sensor assembly part.

FIG. 17, shows a sectional schematic representation of part of a base plate 4 and/or a sensor assembly part 700. The base plate 4 and/or the sensor assembly part 700 comprises a first adhesive layer 200, an optional second adhesive layer 202, and a top layer 208. An electrode assembly 204 comprising a plurality of electrodes 216 is arranged between the first adhesive layer 200 and the top layer 208, such as between the first adhesive layer 200 and the second adhesive layer 202. For example, a second part of the electrode assembly 204 is arranged between the first adhesive layer and the second adhesive layer 202/the top layer 208. Although not illustrated, the electrode assembly 204 may comprise a reinforcement element 308, e.g. as illustrated in FIGS. 15 and 16. Thus, the base plate 4 and/or the sensor assembly part 700 of FIG. 17 may correspond to the base plate 4 and/or the sensor assembly part 700, respectively, of FIGS. 15 and 16.

The first part 302 of the electrode assembly 204, together with the top layer 208 and the optional second adhesive layer, has been turned over to expose the connection parts 217 of the plurality of electrodes 216 on a distal side of the base plate 4 and/or the sensor assembly part 700. Thus, the primary side of the first part 302 initially being a proximal side (as shown in FIG. 15) is, after the first part 302 has been turned, facing distally.

Figure 18:
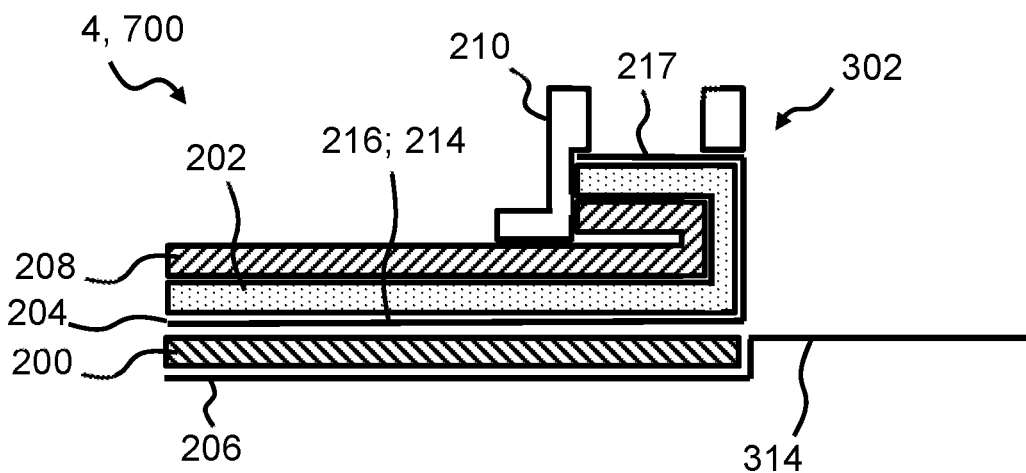
FIG. 18 shows a schematic representation of part of a base plate and/or a sensor assembly part.

FIG. 18, shows a sectional schematic representation of part of a base plate 4 and/or a sensor assembly part 700 as shown in FIG. 17, wherein the base plate 4 and/or the sensor assembly part 700 comprises a coupling part 210. The coupling part 210 is configured for forming a mechanical connection between the monitor device and the base plate 4 and/or the sensor assembly part 700. The first part 302 of the electrode assembly 204 is extending into the coupling part 210, e.g. to allow the monitor device, such as terminals of the monitor device to connect to the electrodes 216 of the base plate 4 and/or the sensor assembly part 700. The coupling part 210 is positioned to cover the connection parts 217 of the plurality of electrodes 216. The coupling part 210 may be attached to the top layer 208 and/or the coupling part 210 may be attached to the electrode assembly 204.

Figure 19:
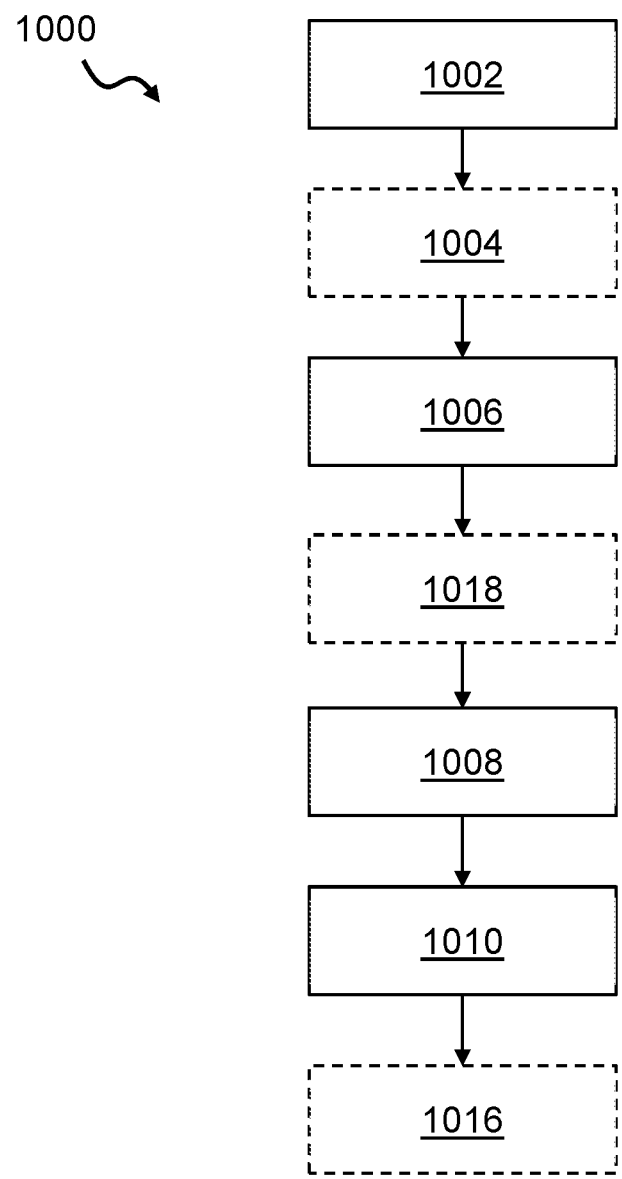
FIG. 19 shows a flowchart of an exemplary method.

FIG. 19 shows a flowchart of an exemplary method 1000, such as a method for manufacturing a base plate or a sensor assembly part for an ostomy appliance. The method comprises providing 1002 a top layer, optionally providing 1004 a second adhesive layer, and providing 1006 an electrode assembly comprising a plurality of electrodes, the electrode assembly having a first part and a second part, the first part comprising connection parts of the plurality of electrodes. The method further comprises: providing 1008 a first adhesive layer, assembling 1010 the top layer, the optional second adhesive layer, the electrode assembly and the first adhesive layer. The first adhesive layer being provided 1008 such that a primary side of the first part of the electrode assembly is not covered by the first adhesive 1008.

Assembling 1010 the top layer, the optional second adhesive layer, the electrode assembly and the first adhesive layer includes assembling such that the electrode assembly is arranged between the first adhesive layer and the top layer and/or between the first adhesive layer and the optional second adhesive layer. For example, assembling 1010 the top layer, the optional second adhesive layer, the electrode assembly and the first adhesive layer includes assembling such that the second part of the electrode assembly, e.g. comprising sensing parts of the plurality of electrodes, is arranged between the first adhesive layer and the second adhesive layer/the top layer.

The method 1000 furthermore optionally comprises providing 1016 a coupling part on the base plate or sensor assembly part. The coupling part may be provided 1016 to be aligned with the top layer opening and the optional second adhesive layer opening. The coupling part may be provided 1016 to be aligned with the first part of the electrode assembly.

The method 1000 furthermore optionally comprises providing 1018 a release liner. The first adhesive layer may be provided 1008 on the release liner. For example, the first adhesive layer may be provided 1008, such as formed, on the release liner by scraping of a first composition, such as a first adhesive composition. The release liner may comprise a first elevated part for forming an area not covered by the first adhesive layer. The first elevated part and consequently the area not covered by the first adhesive layer may be aligned with the first part of the electrode assembly, such that the first adhesive layer does not cover the first part of the electrode assembly.

The position of the first connector on the base plate and/or the sensor assembly part, the number of terminals and the position of the terminals in the coupling part may be adapted to the electrode configuration used in the electrode assembly of the base plate and/or the sensor assembly part.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Exemplary embodiments of the present disclosure are set out in the following items:

1. Method for manufacturing a base plate or a sensor assembly part for an ostomy appliance, the method comprising:
   providing a top layer;
   providing an electrode assembly comprising a plurality of electrodes, the electrode assembly having a first part and a second part, the first part comprising connection parts of the plurality of electrodes;
   providing a first adhesive layer; and
   assembling the top layer, the electrode assembly and the first adhesive layer, such that the second part of the electrode assembly is arranged between the first adhesive layer and the top layer, wherein the first adhesive layer is provided such that a primary side of the first part of the electrode assembly is not covered by the first adhesive.

2. Method according to item 1 comprising providing a release liner, and wherein the first adhesive layer is provided on the release liner.

3. Method according to item 2, wherein the release liner comprises a first elevated part and the first adhesive layer is provided on the release liner by scraping a first composition onto the release liner, the first elevated part providing an exempt area of the release liner whereon the first adhesive composition is not disposed, the exempt area being aligned with the first part of the electrode assembly.

4. A base plate for an ostomy appliance, the base plate comprising:
   a top layer;
   a first adhesive layer; and
   an electrode assembly comprising a plurality of electrodes, the electrode assembly having a first part and a second part, the first part comprising connection parts of the plurality of electrodes, the second part being arranged between the first adhesive layer and the top layer;
   a monitor interface configured for connecting the base plate to a monitor device, the monitor interface comprising a plurality of terminals configured to form electrical connections with respective terminals of the monitor device,
wherein the first adhesive layer is not covering a primary side of the first part of the electrode assembly.

5. The base plate of item 4, wherein the connection parts forms the plurality of terminals of the monitor interface.
6. The base plate of any of items 4-5, wherein the plurality of electrodes is provided on a proximal side of the electrode assembly.
7. The base plate of item 6, wherein the first part of the electrode assembly is turned over to expose the connection parts of the plurality of electrodes on a distal side of the base plate.
8. The base plate of any of items 4-7, wherein the monitor interface comprises a coupling part configured for forming a mechanical connection, such as a releasable coupling, between the monitor device and the base plate.
9. The base plate of item 8, wherein the coupling part is attached to the top layer, such as a distal side of the top layer.
10. The base plate of item 9 as dependent on item 7, wherein the coupling part is positioned to cover the connection parts of the plurality of electrodes.
11. The base plate of items 4-10, wherein the electrode assembly comprises a reinforcement element, and wherein the reinforcement element is forming at least part of the first part of the electrode assembly.
12. The base plate of item 11, wherein the reinforcement element comprises a plurality of conductive paths connected to the plurality of electrodes to form the connection parts of the plurality of electrodes.
13. The base plate of any of items 11 or 12, wherein the reinforcement element is a flex circuit.
14. The base plate of any of items 4-13 comprising a second adhesive layer between the top layer and the electrode assembly.
15. A base plate for an ostomy appliance obtainable by the method according to any of items 1-3.
16. A sensor assembly part for an ostomy appliance, the sensor assembly part comprising:
    a top layer;
    a first adhesive layer; and
    an electrode assembly comprising a plurality of electrodes, the electrode assembly having a first part and a second part, the first part comprising connection parts of the plurality of electrodes, the second part being arranged between the first adhesive layer and the top layer;
    a monitor interface configured for connecting the sensor assembly part to a monitor device, the monitor interface comprising a plurality of terminals configured to form electrical connections with respective terminals of the monitor device,
wherein the first adhesive layer is not covering a primary side of the first part of the electrode assembly.
17. The sensor assembly part of item 16, wherein the connection parts forms the plurality of terminals of the monitor interface.
18. The sensor assembly part of any of items 16-17, wherein the plurality of electrodes is provided on a proximal side of the electrode assembly.
19. The sensor assembly part of item 18, wherein the first part of the electrode assembly is turned over to expose the connection parts of the plurality of electrodes on a distal side of the sensor assembly part.
20. The sensor assembly part of any of items 16-19, wherein the monitor interface comprises a coupling part configured for forming a mechanical connection, such as a releasable coupling, between the monitor device and the sensor assembly part.
21. The sensor assembly part of item 20, wherein the coupling part is attached to the top layer, such as a distal side of the top layer.
22. The sensor assembly part of item 21 as dependent on item 7, wherein the coupling part is positioned to cover the connection parts of the plurality of electrodes.
23. The sensor assembly part of items 16-22, wherein the electrode assembly comprises a reinforcement element, and wherein the reinforcement element is forming at least part of the first part of the electrode assembly.
24. The sensor assembly part of item 23, wherein the reinforcement element comprises a plurality of conductive paths connected to the plurality of electrodes to form the connection parts of the plurality of electrodes.
25. The sensor assembly part of any of items 23 or 24, wherein the reinforcement element is a flex circuit.
26. The sensor assembly part of any of items 16-25 comprising a second adhesive layer between the top layer and the electrode assembly.
27. A sensor assembly part for an ostomy appliance obtainable by the method according to any of items 1-3.

LIST OF REFERENCES 1 ostomy system
2 ostomy appliance
4 base plate
6 monitor device
8 accessory device
10 server device
12 network
14 coupling member
16 coupling ring
18 stoma-receiving opening
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
122 antenna
124 wireless transceiver
126 loudspeaker
128 haptic feedback element
200 first adhesive layer
200A distal side/surface of first adhesive layer
200B proximal side/surface of first adhesive layer
202 second adhesive layer
202A distal side/surface of second adhesive layer
202B proximal side/surface of second adhesive layer
204 electrode assembly
204A distal side/surface of electrode assembly
204B proximal side/surface of electrode assembly
206 release liner
206A distal side/surface of the release liner
206B proximal side/surface of the release liner
208 top layer
208A distal side/surface of the top layer
208B proximal side/surface of the top layer 209 coupling ring
210 coupling part of first connector
211 first connector
212 terminals of first connector
213 first intermediate element
213A distal side/surface of first intermediate element
213B proximal side/surface of first intermediate element
214 support layer of electrode assembly
214A distal side/surface of support layer
214B proximal side/surface of support layer
216 electrodes of electrode assembly
217 connection parts
218 masking element
218A distal side/surface of masking element
218B proximal side/surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
270 terminal interface region
272 terminal element(s)
272A distal end of terminal element(s)
272B proximal end of terminal element(s)
274A distal part of terminal element(s)
274B proximal part of terminal element(s)
276A distal terminal element bend
276B proximal terminal element bend
278 guide hole
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
302 first part of electrode assembly
303 second part of electrode assembly
308 reinforcement element
308A distal side of reinforcement element
308B proximal side of reinforcement element
310 openings
311 conductive paths
314 first elevated part
700 sensor assembly part
1000 method
1002 providing top layer
1004 providing second adhesive layer
1006 providing electrode assembly
1008 providing first adhesive layer
1010 assembling layers
1016 providing coupling part
1018 providing release liner
M number of terminals in the first interface of the monitor device

The invention claimed is:

1. A sensing accessory for detecting leakage in an ostomy device, the sensing accessory comprising:
an adhesive layer attachable to skin of a user;
a sensor region disposed distal to the adhesive layer, the sensor region comprising a plurality of electrodes providing a plurality of sensors configured to be arranged around a stoma-receiving opening of an ostomy base plate that is attachable to the sensing accessory, wherein the plurality of electrodes comprises a first electrode arranged at a different radial distance from the stoma-receiving opening than a second electrode;
a connector connected at a first end to the plurality of electrodes and extending to a second terminal end of the connector; and
a reinforcement element attached to the connector and comprising a conductive path;
wherein the conductive path allows electrical communication between the plurality of sensors and an external monitor device that is attachable to the conductive path of the reinforcement element.

2. The sensing accessory of claim 1, wherein the plurality of electrodes comprises a first part and a second part;
wherein the first part comprises connection parts in electrical communication with the conductive path of the reinforcement element and in electrical communication with the plurality of electrodes wherein the adhesive layer does not cover the first part of the plurality of electrodes.

3. The sensing accessory of claim 1, wherein the plurality of electrodes is formed in an arc around at least a portion of the stoma-receiving opening, with the first electrode located in a first arc at a first radial distance from the stoma-receiving opening and the second electrode is disposed in a second arc at a second radial distance from the stoma-receiving opening.

4. The sensing accessory of claim 1, wherein the plurality of electrodes are printed as circular arcs around the stoma-receiving opening.

5. The sensing accessory of claim 1, wherein the plurality of electrodes of the plurality of sensors comprises conductive ink printed along a curved arc around the stoma-receiving opening.

6. The sensing accessory of claim 1, wherein the connector is a tail that extends radially away from the plurality of electrodes and radially away from the adhesive layer to a tail end, and tail is configured to bend away from the ostomy base plate for connection with the external monitor device.

7. The sensing accessory of claim 1, wherein the reinforcement element is configured for mechanical and electrical connection to the external monitor device.

8. The sensing accessory of claim 1, wherein the plurality of electrodes of the plurality of sensors comprises:
a first electrode pair located at a first radial distance from the stoma-receiving opening;
a second electrode pair located at a second radial distance from the stoma-receiving opening;
a third electrode pair located at a third radial distance from the stoma-receiving opening, with the first radial distance closer to the stoma-receiving opening than the third radial distance is from the stoma-receiving opening;
wherein the connector is connected at the first end to the first electrode pair, the second electrode pair, and the third electrode pair;
wherein an electrical resistance value measured at the first electrode pair, the second electrode pair, and the third electrode pair provides moisture propagation information relative to the stoma-receiving opening.

9. The sensing accessory of claim 1, further comprising:
a first sensor point opening formed in the adhesive layer and located at a first position around a circumference of the stoma-receiving opening;
a second sensor point opening formed in the adhesive layer and located at a second position around the circumference of the stoma-receiving opening; and
a third sensor point opening formed in the adhesive layer and located at a third position around the circumference of the stoma-receiving opening, with the first position different from the second position and the second position different from both the first position and the third position;
wherein an electrical resistance value measured at each of the first sensor point opening, the second sensor point opening, and the third sensor point opening provides moisture propagation information relative to different circumferential locations around the stoma-receiving opening.

10. A sensor for determining moisture propagation relative to a stoma of a user, the sensor comprising:
a plurality of electrodes provided on a sensing accessory that is attachable to an ostomy base plate, the plurality of electrodes providing a plurality of sensors configured to be arranged around a stoma-receiving opening of the ostomy base plate, wherein the plurality of electrodes includes electrodes arranged at different radial distances from the stoma-receiving opening, comprising:
a first electrode located at a first radial distance from the stoma-receiving opening,
a second electrode located at a second radial distance from the stoma-receiving opening,
a third electrode located at a third radial distance from the stoma-receiving opening, with the first radial distance closer to the stoma-receiving opening than the third radial distance is from the stoma-receiving opening;
a connector connected at a first end to the first electrode, the second electrode, and the third electrode;
a reinforcement element connected to the connector and comprising an electrically conductive path, the reinforcement element provided to allow electrical connection between the plurality of electrodes and an external monitor device attachable to the electrically conductive path;
wherein a measurement of an electrical resistance value for each of the first electrode, the second electrode, and the third electrode provides moisture propagation information relative to the stoma-receiving opening.

11. He sensor of claim 10, wherein the first electrode, the second electrode, and the third electrode are disposed between an adhesive layer of the sensing accessory that is attachable to skin of a user and a top layer of the sensing accessory that is attachable to the ostomy base plate,
wherein the reinforcement element of the connector is bendable and available for mechanical and electrical connection to the external monitor device.

12. The sensing accessory of claim 10, wherein the plurality of sensors comprises:
a first sensor aligned with a first sensor point opening of the sensing accessory and located at a first position around a circumference of the stoma-receiving opening;
a second sensor aligned with a second sensor point opening of the sensing accessory and located at a second position around the circumference of the stoma-receiving opening; and
a third sensor aligned with a third sensor point opening of the sensing accessory and located at a third position around the circumference of the stoma-receiving opening, with the first position different from the second position and the second position different from both the first position and the third position;
wherein a measurement of an electrical resistance value measured at each of the first sensor point opening the second sensor point opening, and the third sensor point opening provides moisture propagation information relative to different circumferential locations around the stoma-receiving opening.

13. The sensing accessory of claim 10, wherein:
the first electrode comprises a first electrode pair located at the first radial distance from the stoma-receiving opening;
the second electrode comprises a second electrode pair located at the second radial distance from the stoma-receiving opening,
the third electrode comprises a third electrode pair located at the third radial distance from the stoma-receiving opening; with the first radial distance closer to the stoma-receiving opening than the third radial distance is from the stoma-receiving opening;
wherein the connector is connected at the first end to the first electrode pair, the second electrode pair, and the third electrode pair with the connector extending in a radial direction to the reinforcement element.

14. The sensing accessory of claim 1, wherein the adhesive layer is disposed on a proximal side of the sensing accessory and the reinforcement element is attached distal relative to the adhesive layer.

15. The sensing accessory of claim 1, wherein the conductive path is provided by openings formed in the reinforcement element, with the openings electrically communicating with the plurality of electrodes.

16. The sensing accessory of claim 1, wherein connector is a flexible circuit and the conductive path is provided by a plurality of conductive paths each electrically connected with one of the plurality of electrodes.

17. A sensing accessory for detecting leakage in an ostomy device, the sensing accessory comprising:
- an adhesive layer disposed on a proximal side of the sensing accessory and attachable to skin of a user;
- a sensor region disposed distal to the adhesive layer, the sensor region comprising a plurality of electrodes providing a plurality of sensors configured to be arranged around a stoma-receiving opening of an ostomy base plate that is attachable to a distal side of the sensing accessory, wherein the plurality of electrodes comprises a first electrode arranged at a different radial distance from the stoma-receiving opening than a second electrode;
- a connector comprising a conductive path communicating with the plurality of electrodes;
- wherein the conductive path allows electrical communication between the plurality of sensors and an external monitor device attachable to the connector; and
- a first sensor point opening formed as a first void in the adhesive layer and located at the first electrode;
- a second sensor point opening formed as a second void in the adhesive layer and located at the second electrode;
- wherein an electrical resistance value for the first electrode measured at the first sensor point opening and for the second electrode measured at the second sensor point opening provides moisture propagation information relative to different circumferential locations around the stoma-receiving opening.

18. The sensing accessory of claim 17, wherein the electrical resistance value for the first electrode measured at the first sensor point opening and for the second electrode measured at the second sensor point opening provides moisture propagation information relative to different radial locations around the stoma-receiving opening.

\* \* \* \* \*